(12) United States Patent
Kelly et al.

(10) Patent No.: US 10,881,342 B2
(45) Date of Patent: Jan. 5, 2021

(54) SAMPLING ASSEMBLY

(71) Applicant: ATOMO DIAGNOSTICS PTY LIMITED, Drummoyne (AU)

(72) Inventors: John Kelly, Newington (AU); Richard Sokolov, Newington (AU); Ian Fredrick Johnson, Newington (AU); Ernesto Monis Hueso, Newington (AU); Eric Siu, Newington (AU); Melody Shiue, Newington (AU); Kamman Law, Newington (AU); Johannes Behrisch, Newington (AU)

(73) Assignee: ATOMO DIAGNOSTICS PTY LIMITED, Drummoyne (AU)

( * ) Notice: Subject to any disclaimer, the term of this patent is extended or adjusted under 35 U.S.C. 154(b) by 850 days.

(21) Appl. No.: 14/180,751

(22) Filed: Feb. 14, 2014

(65) Prior Publication Data

US 2014/0236044 A1 Aug. 21, 2014

Related U.S. Application Data

(63) Continuation of application No. 13/879,297, filed as application No. PCT/AU2011/001321 on Oct. 17, 2011.

(51) Int. Cl.
*A61B 5/15* (2006.01)
*A61B 5/151* (2006.01)
*A61B 5/157* (2006.01)

(52) U.S. Cl.
CPC ........ *A61B 5/150213* (2013.01); *A61B 5/157* (2013.01); *A61B 5/1519* (2013.01);
(Continued)

(58) Field of Classification Search
CPC ........ A61B 5/150213; A61B 5/150618; A61B 5/150717; A61B 5/150503; A61B 5/1519; A61B 5/150358; A61B 5/15113; A61B 5/150549; A61B 5/15117; A61B 5/150412; A61B 5/157; A61B 5/150022
See application file for complete search history.

(56) References Cited

U.S. PATENT DOCUMENTS 4,637,403 A 1/1987 Garcia et al.
4,661,319 A 4/1987 Lape
(Continued)

FOREIGN PATENT DOCUMENTS

CN 101641052 1/2013
EP 1284121 2/2003
(Continued)

OTHER PUBLICATIONS

Supplementary Partial European Search Report dated Jan. 31, 2014 in EP Application No. 11 75 5574. (7 pages).
(Continued)

*Primary Examiner* — Rene T Towa
(74) *Attorney, Agent, or Firm* — Shutts & Bowen LLP

(57) ABSTRACT

An assembly for sampling bodily fluid, the assembly comprising a membrane penetration device comprising a membrane penetrating element for penetrating a bodily membrane to release a bodily fluid; and, a collector configured in a collection position to take up the released bodily fluid and retain the fluid for delivery to a test element.

10 Claims, 20 Drawing Sheets

(52) U.S. Cl.
CPC .... *A61B 5/150022* (2013.01); *A61B 5/15113* (2013.01); *A61B 5/15117* (2013.01); *A61B 5/150358* (2013.01); *A61B 5/150412* (2013.01); *A61B 5/150503* (2013.01); *A61B 5/150549* (2013.01); *A61B 5/150618* (2013.01); *A61B 5/150717* (2013.01)

(56) References Cited

U.S. PATENT DOCUMENTS

| | | | |
|---|---|---|---|
| 5,096,669 | A | 3/1992 | Lauks et al. |
| 5,249,584 | A | 10/1993 | Karkar et al. |
| 5,714,390 | A | 2/1998 | Hallowitz et al. |
| 5,879,311 | A * | 3/1999 | Duchon ............. A61B 5/14532 600/573 |
| 6,264,619 | B1 | 7/2001 | Ferguson |
| 6,634,243 | B1 * | 10/2003 | Wickstead ............. B01L 3/502 422/417 |
| 6,830,551 | B1 | 12/2004 | Uchigaki et al. |
| 7,885,697 | B2 | 2/2011 | Brister et al. |
| 7,946,984 | B2 | 5/2011 | Brister et al. |
| 8,229,534 | B2 | 7/2012 | Brister et al. |
| 2002/0002344 | A1 | 1/2002 | Douglas et al. |
| 2002/0150501 | A1 | 10/2002 | Robertson et al. |
| 2003/0013121 | A1 | 1/2003 | Khan |
| 2005/0283094 | A1 | 12/2005 | Thym et al. |
| 2006/0052724 | A1 * | 3/2006 | Roe .................... A61B 5/14532 600/583 |
| 2006/0100542 | A9 * | 5/2006 | Wong ................. A61B 5/15125 600/583 |
| 2006/0127886 | A1 | 6/2006 | Kaylor et al. |
| 2007/0100213 | A1 | 5/2007 | Dossas et al. |
| 2007/0299365 | A1 * | 12/2007 | Calasso ............. A61B 5/14532 600/583 |
| 2008/0319347 | A1 | 12/2008 | Keren |
| 2010/0036282 | A1 | 2/2010 | List et al. |
| 2010/0184126 | A1 | 7/2010 | Rutty et al. |
| 2010/0286561 | A1 | 11/2010 | List et al. |
| 2011/0039261 | A1 | 2/2011 | Hillerbrand et al. |
| 2011/0105951 | A1 | 5/2011 | Bernstein et al. |
| 2011/0144465 | A1 | 6/2011 | Shults et al. |
| 2011/0190614 | A1 | 8/2011 | Brister et al. |
| 2012/0283543 | A1 | 11/2012 | Brauker et al. |

FOREIGN PATENT DOCUMENTS

| | | |
|---|---|---|
| EP | 1374770 | 1/2004 |
| JP | 2012505639 | 3/2012 |
| JP | 5127839 | 1/2013 |
| WO | 1988000812 | 2/1988 |
| WO | 2001013795 | 3/2001 |
| WO | 2002010754 | 2/2002 |
| WO | 2002078533 | 10/2002 |
| WO | 2004078232 | 9/2004 |
| WO | 2006037646 | 4/2006 |
| WO | 2007062728 | 6/2007 |
| WO | 2008056363 | 5/2008 |
| WO | 2008085052 | 7/2008 |
| WO | 2008149333 | 12/2008 |
| WO | 2009147680 | 12/2009 |

OTHER PUBLICATIONS

International Search Report dated Apr. 20, 2015 in International Application No. PCT/IB2014/066219. (5 pages).

International Search Report dated Dec. 20, 2011 in International Application No. PCT/AU2011/001321, International Filing Date Oct. 17, 2011. (4 pages).

International Preliminary Report on Patentability dated Jul. 30, 2012 in International Application No. PCT/AU2011/000315, International Filing Date Mar. 18, 2011. (12 pages).

International Search Report dated Jun. 14, 2011 in International Application No. PCT/AU2011/000315, International Filing Date Mar. 18, 2011. (7 pages).

* cited by examiner

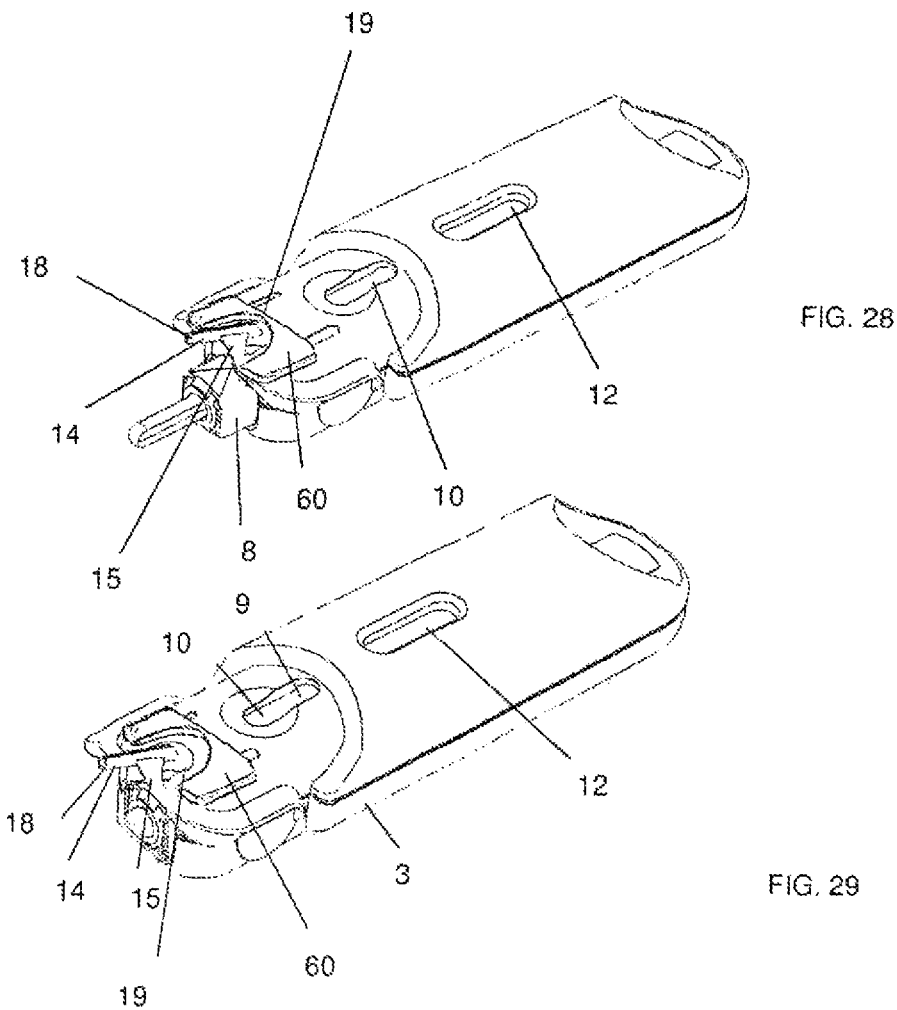
FIG. 28
FIG. 29
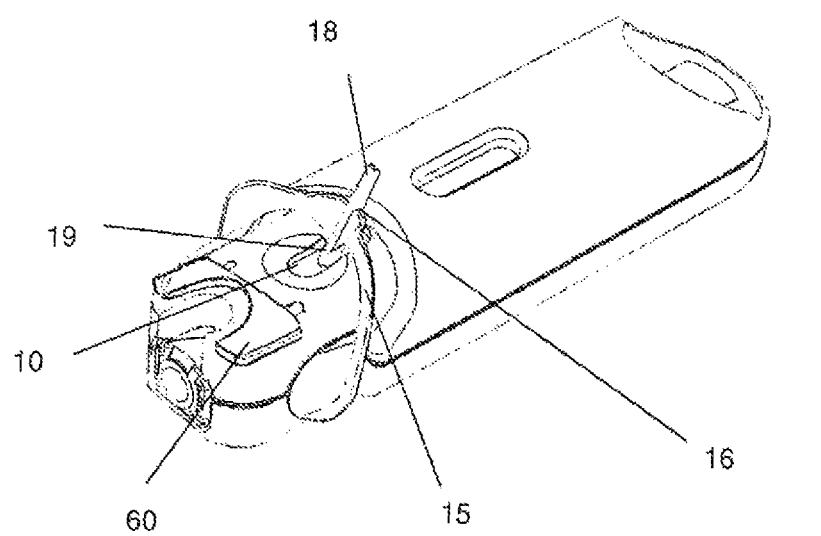
FIG. 30

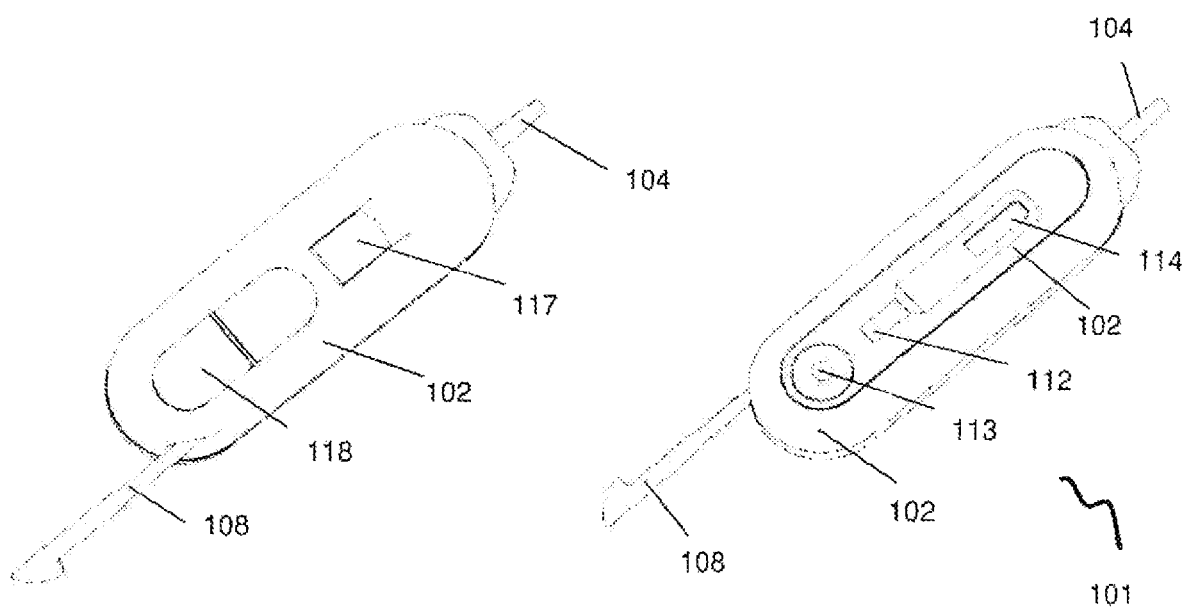

SAMPLING ASSEMBLY

CROSS-REFERENCE TO RELATED APPLICATIONS

This is a continuation of U.S. patent application Ser. No. 13/879,297 filed on Apr. 12, 2013, entitled "SAMPLING ASSEMBLY," which is a 371 National Stage of International Application No. PCT/AU2011/001321, filed on Oct. 17, 2011, entitled "SAMPLING ASSEMBLY," which claims priority to International Australian Application No. 2010904615, filed on Oct. 15, 2010, entitled "SAMPLING ASSEMBLY," the entireties of which are hereby incorporated by reference.

TECHNICAL FIELD

The present invention relates generally to devices and methods for sampling and handling of bodily fluids and performing diagnostics in respect of the bodily fluids.

BACKGROUND OF THE DISCLOSURE

There are many medical conditions in humans and animals for which it is desirable to draw a fluid sample for immediate analysis at the point of sampling. For example, in diagnosis of various diseases, a blood sample drawn from a patient is analyzed for the presence of a blood-borne pathogen. Alternatively a blood sample can be used to determine the presence or absence of healthy levels of specific blood components. Blood samples are also screened for molecular diagnostics to provide diagnosis, classification, detection, monitoring, prognosis or other molecular inference.

Samples taken from a patient, animal or organism may be obtained by penetrating the skin of the user using a piercing, slicing, puncturing, pricking, or cutting element such as a lancet device. A lancet device typically includes a body and a lancet. The body is typically adapted to be held by the user, the lancet being coupled to the body and being adapted to pierce the skin of the patient so as to draw blood therefrom. In some lancet devices, the lancet extends from the body at all times. In other lancet devices, the lancet is adapted to be moved, when actuated, from a retracted position in which the lancet tip is disposed within the body to an extended position in which the lancet tip extends beyond the body. Typically, the movement of the lancet from its retracted position to its extended position is effected with a force that means contact of the moving lancet tap with the skin of a patient results in the penetration of the skin of the patient. In many such lancet devices having a movable lancet, the lancet is automatically drawn back into the body after reaching its extended position in order to minimize the risk of inadvertent lancet sticks.

After the skin, typically of a finger or heel, is penetrated by the lancet, the blood must be expressed from the user and retained for delivery to a test element.

SUMMARY OF THE INVENTION

In some forms, disclosed is an assembly for sampling bodily fluid, the assembly comprising a membrane penetration device comprising a membrane penetrating element for penetrating a bodily membrane to release a bodily fluid; and, a collector configured in a collection position to take up the released bodily fluid and retain the fluid for delivery to a test element. In some forms the collector is configured to take up the released bodily fluid by capillary action.

In some forms disclosed is a collector for taking up and retaining a bodily fluid, the collector configured to be engaged with a membrane penetration device including a membrane penetrating element for penetrating a bodily membrane to release a bodily fluid, the collector adapted in a collection position to take up the released fluid and retain the fluid for delivery to a test element. In some forms the collector is configured to take up the released bodily fluid by capillary action. In some forms the collector is configured to take up fluid through a pressure differential. In some forms the collector is configured to take up the released bodily fluid by suction. In some forms the collector is configured to take up the released bodily fluid, through application of a force.

The foregoing summary is illustrative only and is not intended to be in any way limiting. In addition to the illustrative aspects, embodiments, and features described above, further aspects, embodiments and features will become apparent by reference to the drawings and the following detailed description.

BRIEF DESCRIPTION OF THE DRAWINGS

A preferred embodiment will now be described by way of example only, with reference to the accompanying drawings in which:

FIG. 2.4 is a cut away perspective view of the assembly of FIG. 20;

FIG. 28 is a perspective view of a sixth embodiment of an assembly;

FIG. 29 is a perspective view of the assembly of FIG. 28;

FIG. 30 is a perspective view of the assembly of FIG. 28;

FIG. 44 is a top isometric view of the assembly of FIG. 41;

FIG. 45 is a bottom isometric view of the assembly of FIG. 41.

DETAILED DESCRIPTION OF EMBODIMENTS

Figure 1:
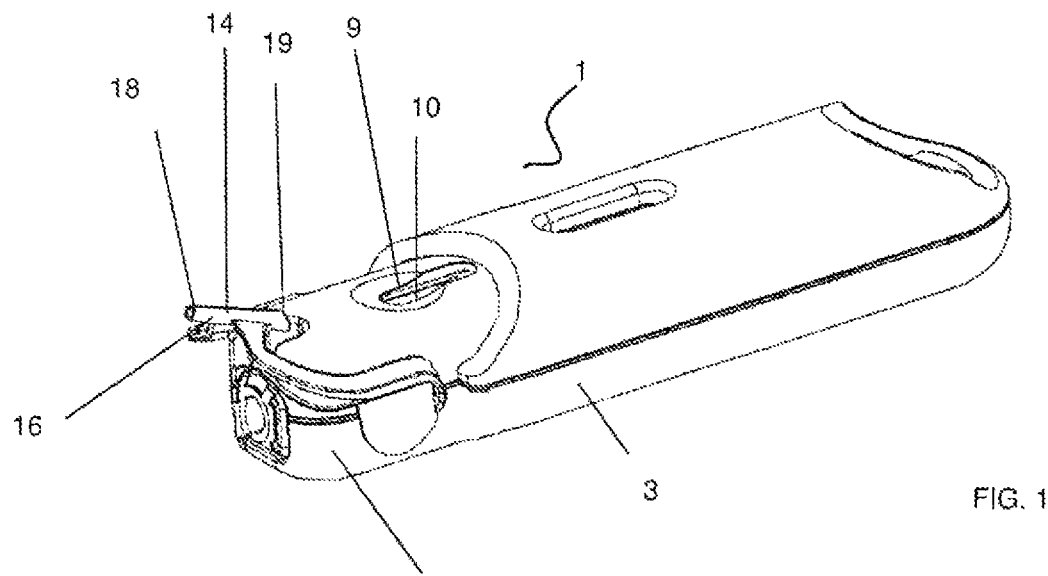
FIG. 1 is a perspective view of one embodiment of an assembly.
Figure 2:
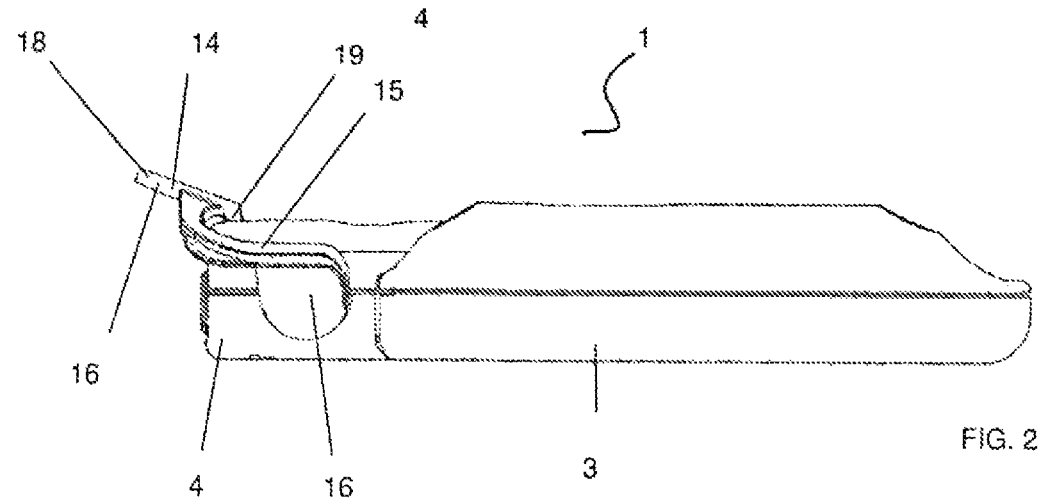
FIG. 2 is a side view of the assembly of FIG. 1.
Figure 3:
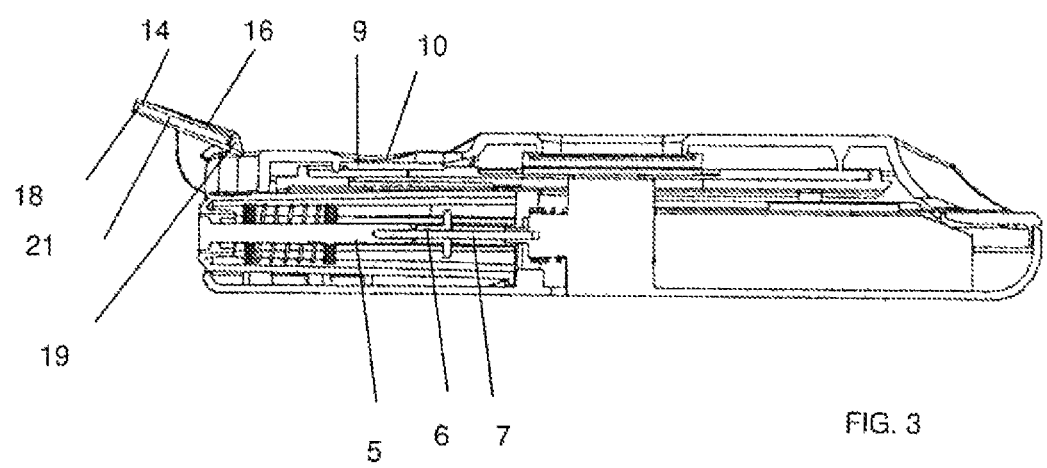
FIG. 3 is a cross-sectional view of the assembly of FIG. 1.

In the following detailed description, reference is made to accompanying drawings which form a part of the detailed description. The illustrative embodiments described in the detailed description, depicted in the drawings and defined in the claims, are not intended to be limiting. Other embodiments may be utilised and other changes may be made without departing from the spirit or scope of the subject matter presented. It will be readily understood that the aspects of the present disclosure, as generally described herein and illustrated in the drawings can be arranged, substituted, combined, separated and designed in a wide variety of different configurations, all of which are contemplated in this disclosure.

This disclosure is directed generally to an assembly for sampling bodily fluids. While the assembly has been frequently described with reference to a lancet, it will be clear to a person skilled in the art that alternatives are available.

In some forms disclosed is an assembly for sampling bodily fluid, the assembly comprising a membrane penetration device comprising a membrane penetrating element for penetrating a bodily membrane to release a bodily fluid; and, a collector configured in a collection position to take up the released bodily fluid and retain the fluid for delivery to a test element.

In some forms the collector is configured to take up the released bodily fluid by capillary action. In some forms the collector is configured to take up fluid through a pressure differential. In some forms the collector is configured to take up the released bodily fluid by suction. In some forms the collector is configured to take up the released bodily fluid through application of a force.

In some forms the collector comprises a body defining a cavity configured to generate capillary action.

In some forms the collector includes a capillary channel. In some forms the capillary channel is a closed channel. In some forms the capillary channel is an open channel.

In some forms the collector comprises a tube.

In some forms the tube extends between an collection opening and a release opening and is tapered toward the collection opening.

In some forms the assembly includes a housing which houses the membrane penetration device and the tube is angled with respect to the housing.

In some forms the collector comprises two substantially parallel plates.

In some forms the collector is moveably engaged with the body

In some forms the collector is pivotably engaged with the body

In some forms the assembly includes a test element and the collector is moveable between the collection position and a delivery position in which the retained fluid is releasable so as to contact the test element.

In some forms in the delivery position the fluid is in contact with the test element and the collector.

In some forms the collector comprises at least one opening which, in the delivery position, is in contact with the test element.

In some forms the opening is proximal to the test element.

In some forms the assembly comprises a housing and the membrane penetrating element is actuatable to adopt an actuated position in which the membrane penetrating element extends beyond the housing.

In some forms the membrane penetrating element is configured to adopt a retracted position in which the membrane penetrating element is located within the housing after actuation.

In some forms the collector is inhibited from moving into the delivery position until the membrane penetrating element is actuated.

In some forms the collector includes a ventilation aperture.

In some forms the collector comprises a tube extending between two openings and a ventilation aperture is positioned intermediate the openings.

In some forms the ventilation aperture comprises a slot extending between the openings.

In some forms the collector is configured to take up a predetermined volume of fluid.

In some forms the predetermined volume of fluid is regulated by a dimensional characteristic of the collector.

In some forms the collector includes an interior cavity and the predetermined volume of fluid is regulated by the size and shape of the cavity.

In some forms the collector includes at least one opening for uptake of the fluid and wherein the opening is adapted to facilitate fluid uptake.

In some forms the internal surface of the collector is raked toward the opening.

In some forms the collector includes an internal cavity and the internal diameter of the cavity increases toward the opening.

In some forms the collector comprises at least one collection opening for uptake of the released fluid, the assembly further comprising a cover configured to cover the opening.

In some forms the collector is moveable between the collection position and a delivery position and the cover blocks the collection opening in the delivery position.

In some forms the rate of movement of the collector between the collection position and the delivery position is controlled.

In a second aspect, disclosed is a collector for taking up and retaining a bodily fluid, the collector configured to be engaged with a membrane penetration device including a membrane penetrating element for penetrating a bodily membrane to release a bodily fluid, the collector adapted in a collection position to take up the released fluid and retain the fluid for delivery to a test element.

In some forms the collector is configured to take up the released bodily fluid by capillary action.

In some forms the collector comprises a body defining a cavity configured to generate capillary action.

In some forms the collector includes a capillary channel.

In some forms the collector is configured to take up a predetermined volume of fluid.

In some forms the predetermined volume of fluid is regulated by a dimensional characteristic of the collector.

In some forms the collector includes an interior cavity and the predetermined volume of fluid is regulated by the size and shape of the cavity.

In a third aspect, disclosed is an assembly for sampling bodily fluid, the assembly comprising a membrane penetration device comprising a membrane penetrating element for penetrating a bodily membrane to release a bodily fluid; and, a collector configured to take up and retain the released bodily fluid until moved into a delivery position in which the fluid is releasable for delivery to a test element.

In a fourth aspect disclosed is an assembly comprising a membrane penetration device comprising a membrane penetrating element for penetrating a bodily membrane to release a bodily fluid; and, a collector configured in a collection position to take up the released bodily fluid and deliver the fluid to a test element.

In some forms the collector is configured to take up the fluid by capillary action.

In some forms the collector comprises a tube.

In some forms the collector extends between an collection opening and a discharge opening and wherein a ventilation aperture is positioned intermediate the collection opening and the discharge opening.

In some forms the ventilation aperture comprises a slot extending between the collection opening and the discharge opening.

In a fifth aspect, disclosed is an assembly for sampling a bodily fluid, the assembly comprising a membrane penetration device comprising a membrane penetrating element for penetrating a membrane to release a bodily fluid; and, a retainer adapted to retain a collector adapted for taking up the released bodily fluid.

In some forms the retainer comprises a cavity extending into the body.

In some forms the retainer comprises a clip engaged with the body.

In some forms the retainer comprises a pivotable engagement.

In some forms the retainer is adapted to allow a collector to be retained in a position that is accessible for use.

In some forms the retainer is adapted to allow a collector to be retained with respect to the assembly such that the collector is moveable between a retained position and an operative position.

In some forms the retainer is adapted to allow the removal of the collector from the retainer.

In some forms the collector is a capillary tube.

In some forms the collector is a pipette.

In some forms the collector is a reservoir.

In some forms the collector comprises a loop far collecting fluid.

In some forms the assembly further comprises a collector configured to take up bodily fluid and retain it for delivery to a test element, the collector being engaged with the retainer.

In some forms the collector is a capillary tube.

In some forms the collector is removably engaged with the retainer.

In some forms the collector is moveable between a retained position and an operative position. In some forms the collector is pivotable between a retained position and an operative position.

In some forms the collector is adapted to contain a substance. In some forms the substance may be a buffer, a reagent or a physiologically acceptable solution. In some forms the substance may be a fluid. In some forms the substance may be effective to react with the bodily fluid.

In some forms the collector comprises a reservoir for containing a substance.

In a sixth aspect, disclosed is an assembly for sampling bodily fluid, the assembly comprising a membrane penetration device comprising a membrane penetrating element for penetrating a bodily membrane to release a bodily fluid; and, a collector configured to adopt a collection position to take up the released bodily fluid and a delivery position to deliver the fluid to a test element.

In some forms the collector is configured to move between the collection position and the delivery position.

In some forms the movement of the collector between the collection position and the delivery position comprises pivoting.

In some forms the movement of the collector between the collection position and the delivery position comprises sliding.

In some forms the movement of the collector between the collection position and the delivery position comprises translation.

In some forms the movement of the collector between the collection position and the delivery positron comprises a combination of two or more of pivoting, rotating, sliding or translating.

In some forms in the delivery position the collector is in contact with the test element.

In some forms the assembly is configured such that movement of the collector between the collection position and the delivery position is controlled.

In some forms the assembly is configured such that movement of the collector between the collection configuration and the delivery configuration is achieved manually.

In some forms the movement is controlled by means of resistance fit.

In some forms the test element is located within the assembly such that in the delivery position the test element gives under pressure placed on the test element by the collector.

In some forms the membrane is skin and the bodily fluid is blood.

In at least some forms the assembly allows a user to sample a bodily fluid from a penetration site and have the fluid taken up into a collector for delivery to a test element. The test element may be integrated into the assembly or may be a separate device or system. In some forms the volume of fluid taken up can be quantified or regulated through a dimensional characteristic of the collector such as the internal geometry of a channel or cavity extending therethrough. In some forms the assembly limits the formation of bubbles in the collector through use of a ventilation aperture. In some forms the assembly restricts a user from adding additional fluid to the test element during or after discharge. In some forms the assembly allows simple and even one-handed sampling of a bodily fluid.

Referring to the figures, in some forms illustrated in FIGS. 1 through 9, disclosed is an assembly 1 for sampling a bodily fluid. The assembly 1 generally comprises a housing 3 which extends from a penetration end 4 and houses a membrane penetration device 5 incorporating a membrane penetrating element 6. In the illustrated form the membrane penetrating element 6 is in the form of a lancet 7 adapted to be positioned within the housing 3 prior to actuation of the membrane penetration device 5. The membrane penetration device 5 is actuated by contact with actuator 8 which releases the lancet such that the lancet extends beyond the housing 3 and can be utilized to penetrate a bodily membrane such as skin to release a bodily fluid such as blood. After actuation in the illustrated form the lancet retracts back into the housing to protect a user from further sticks.

The housing 3 further houses a test element 9. In the illustrated form the test element 9 comprises a test strip incorporated into the housing 3 and accessible through delivery window 10 however it will be clear to a person skilled in the art that alternative test elements are available to provide a diagnostic, including but not limited to lateral flow test strips, vertical flow test strips, agglutination, solid-phase technologies, microfludics and lab on a chip technologies. The housing further comprises a test results window 12 which allows a user to view the results of a test.

A collector 14 is engaged with the housing 3. In the illustrated form the collector 14 is engaged by means of at least one engagement arm 15 which engages the housing 3 at engagement point 16. The engagement arms 15 are rotatable about an axis centered, on engagement point 16.

Rotation of engagement arms 15 moves the collector 14 with respect to the body 3.

In the illustrated form shown in FIGS. 1 through 9, the collector 14 comprises a capillary tube 17 extending between a collection opening 18 and a discharge opening 19. A channel 21 extends through the capillary tube 17 and is adapted to generate capillary action and take up fluid into the collector 14.

Figure 8:
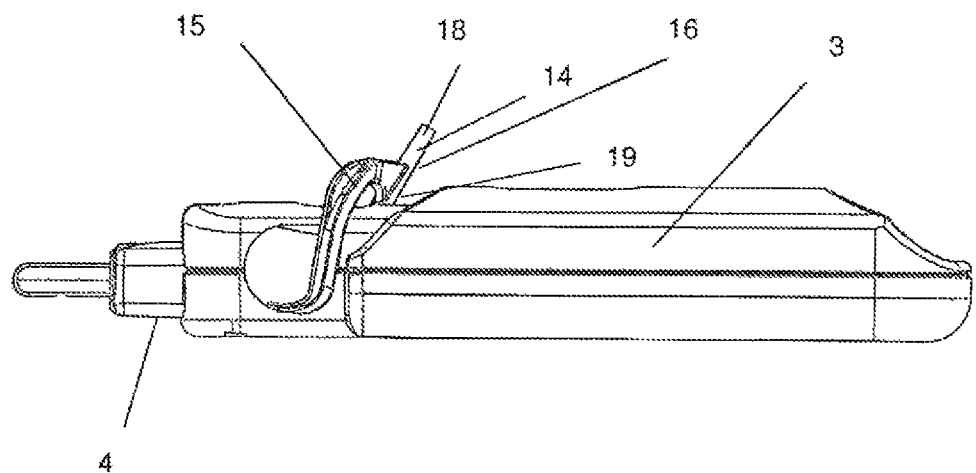
FIG. 8 is a side view of the assembly of FIG. 1.
Figure 9:
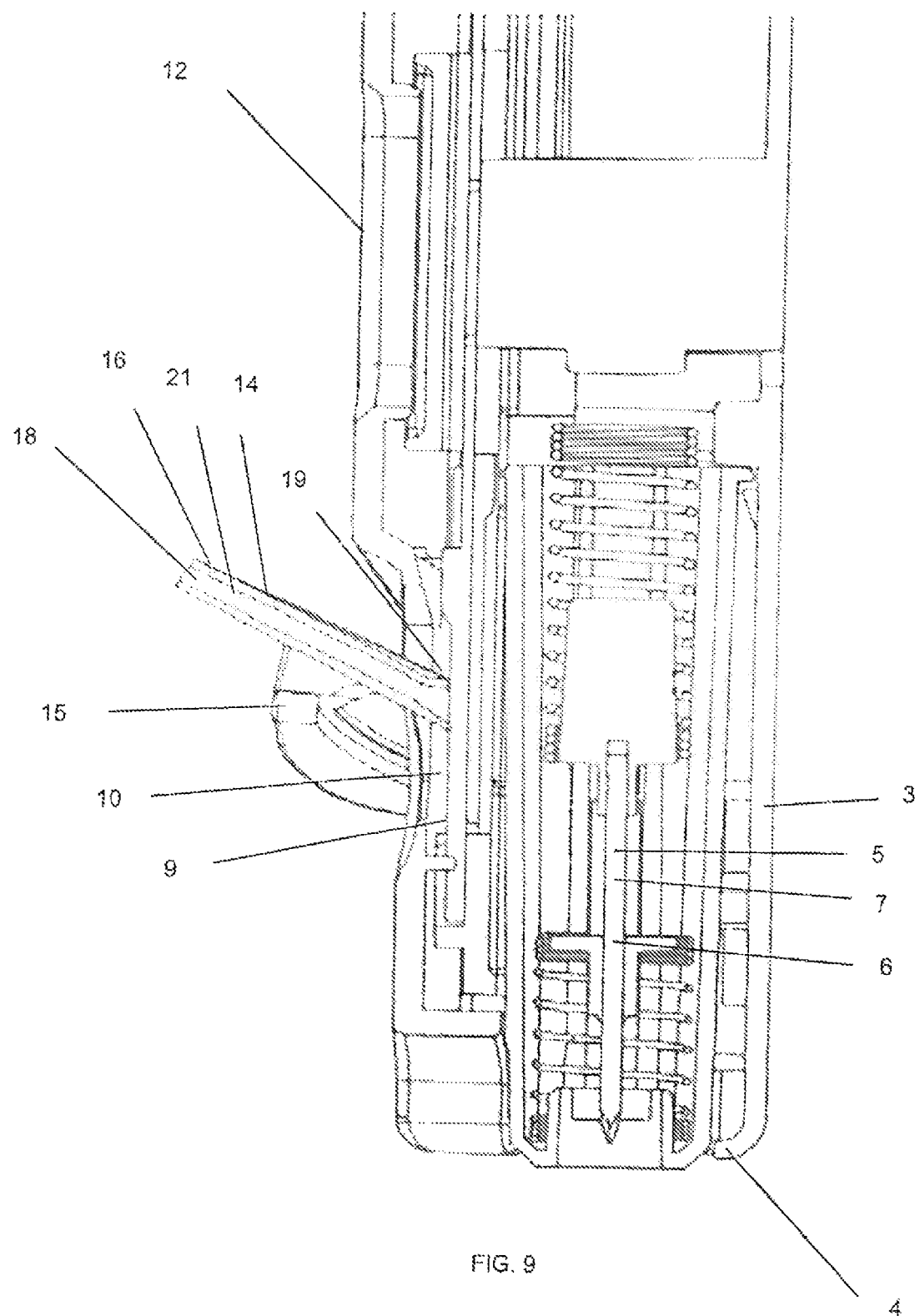
FIG. 9 is a cross-sectional view of the assembly of FIG. 1.

The collector 14 is moveable by rotation of engagement arms 15 from a collection position as shown in FIGS. 1 through 7 to a delivery position as shown in FIGS. 8 and 9. In the collection position the collector extends at an angle with respect to the housing 3 to allow for easy access to the collection opening 18. In this position the discharge opening 19 of the collector 14 is spaced apart from the test element 9 situated behind delivery window 10.

Figure 4:
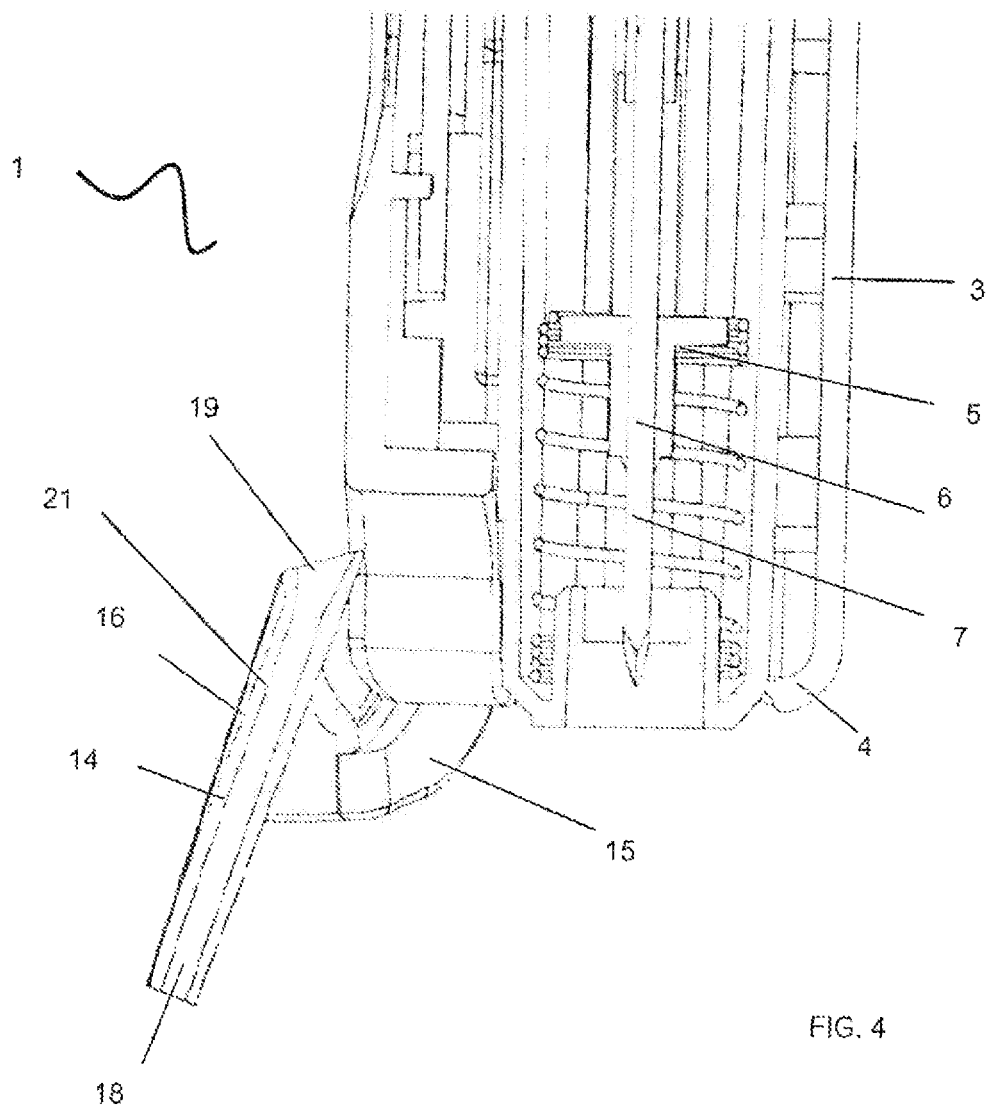
FIG. 4 is a detail cross-sectional view of the assembly of FIG. 1.
Figure 5:
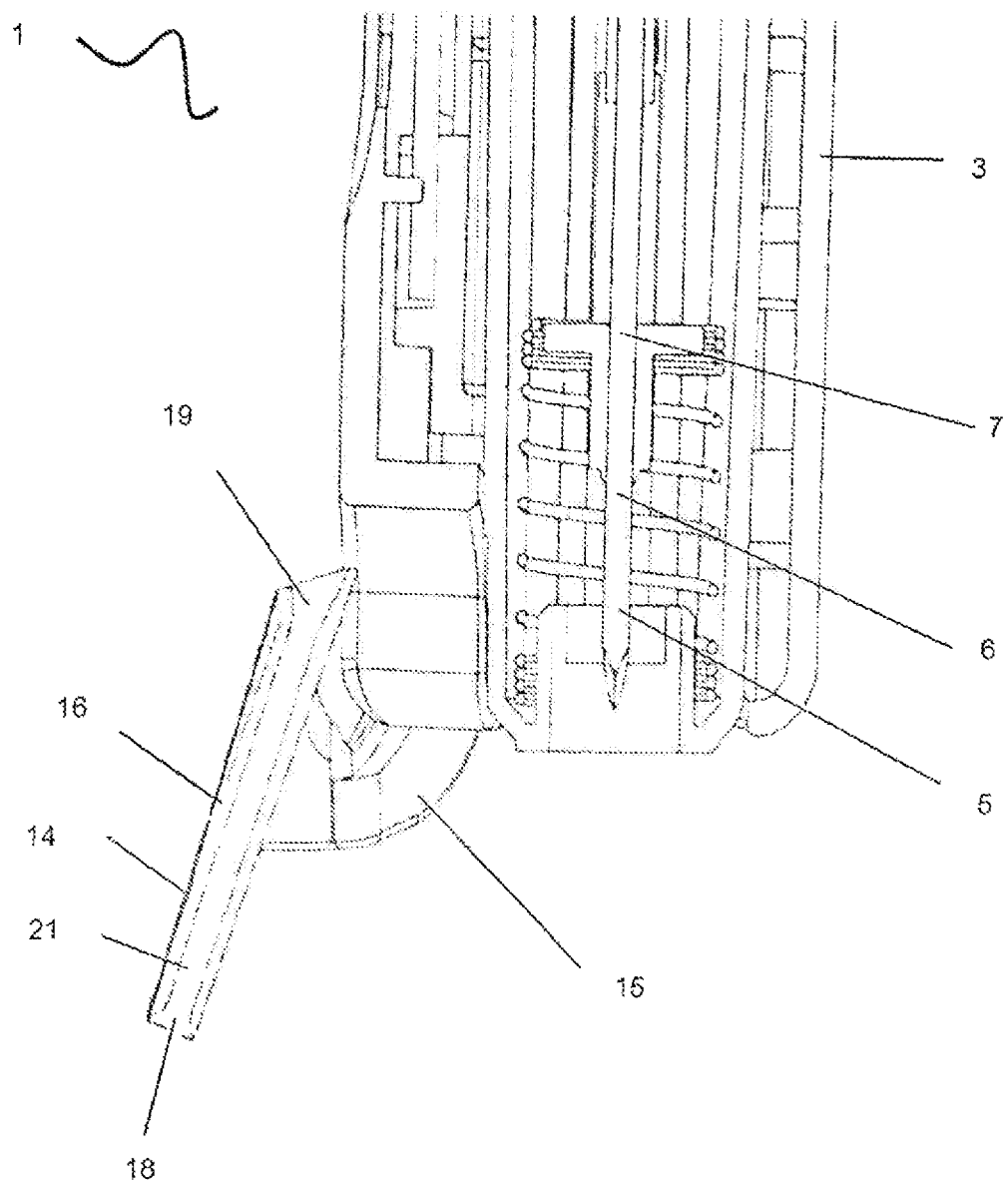
FIG. 5 is a detail, cross-sectional view of a second embodiment of the assembly.
Figure 6:
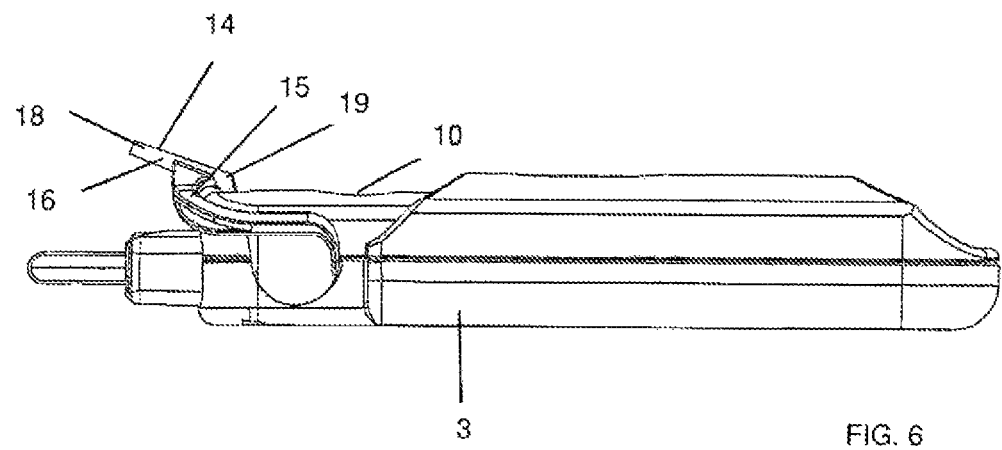
FIG. 6 is a side view of the assembly of FIG. 1.
Figure 7:
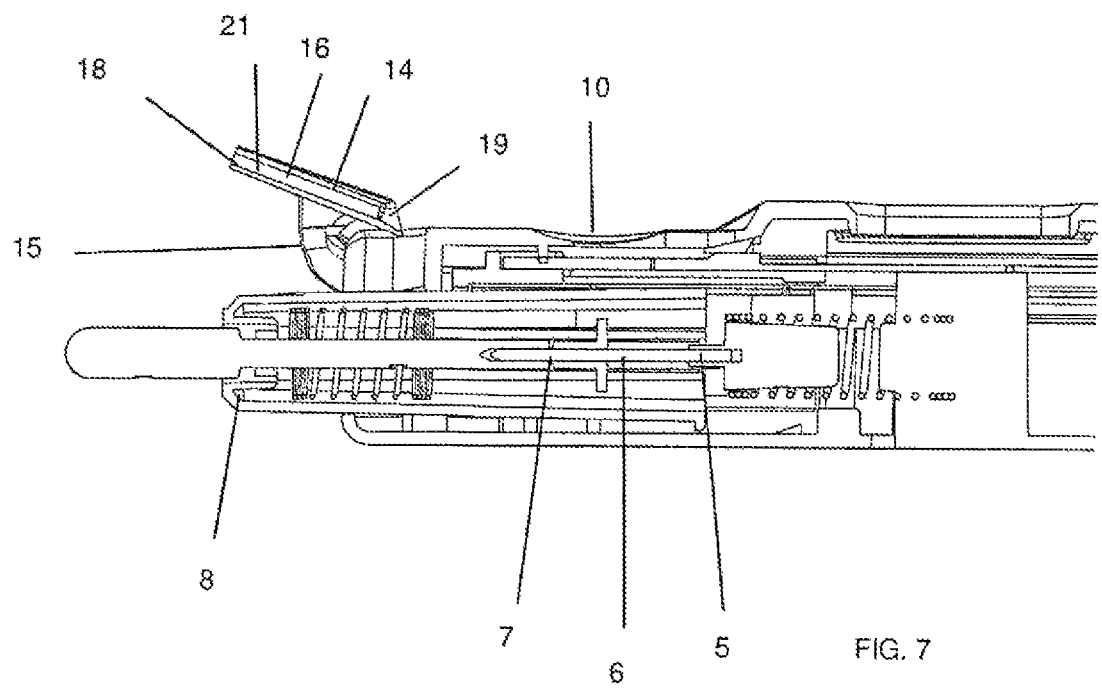
FIG. 7 is a cross-sectional view of the assembly of FIG. 1.

As shown best in FIG. 4 the capillary tube 16 is tapered toward the collection opening 18. As a result of the tapering the tip of the capillary tube presents a small cross-sectional area. This limits the fluid that is in contact with the capillary tube body rather than the internal cavity and promotes movement of fluid into the collector 14 rather than on the surface. In some forms, the internal surface of the capillary tube is raked toward the collection opening 18 as shown in FIG. 5. These features facilitate the uptake of fluid into the collector.

In the illustrated form the collector is sized and shaped to allow a predetermined volume of fluid to be taken up into the capillary tube. The internal geometry including diameter and length of the channel 21 regulates the volume of fluid taken up into the collector 14. Alternatively an indicator can be located on the collector to allow a user to determine the volume of fluid held within the collector 14.

When the collector 14 is moved into the delivery position the discharge opening 19 of the collector 14 contacts the test element 9 to allow release of the fluid retained within the channel 21 in the capillary tubs 16. Fluid is released through wicking away from the point of contact between the collector 14 and the test element 9.

Thus in use a user positions a bodily membrane at the penetration end 4 of the housing and actuates the membrane penetration device 5 such that the lancet 7 pierces the bodily membrane and is retracted again into the housing 3. The user then positions the finger at the collection opening 18 of the collector and bodily fluid is taken up into the collector 14 by capillary action.

The user then moves the collector 14 into the delivery position as shown in FIGS. 8 and 9. In the delivery position the discharge opening 19 contacts the test element s and fluid retained within the collector by capillary action is released onto the test element.

Figure 10:
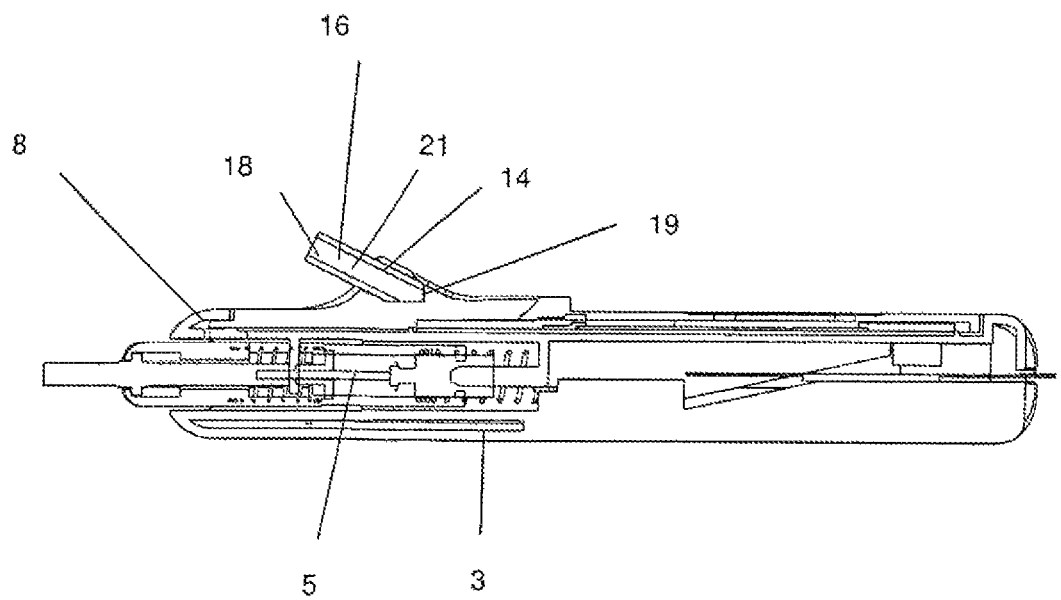
FIG. 10 is a cross-sectional view of a third embodiment of an assembly.
Figure 11:
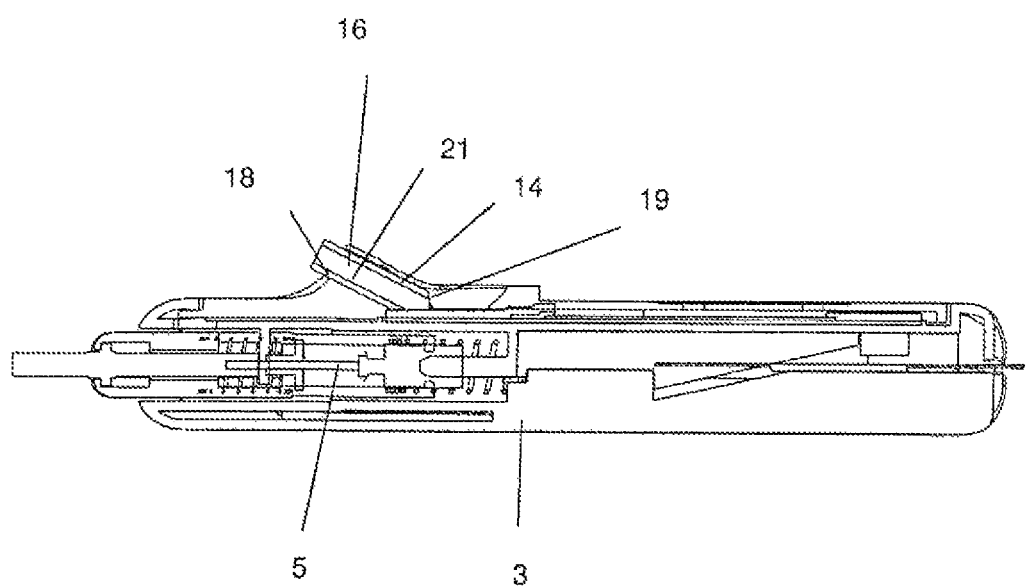
FIG. 11 is a cross-sectional Flew of the assembly of FIG. 10.
Figure 12:
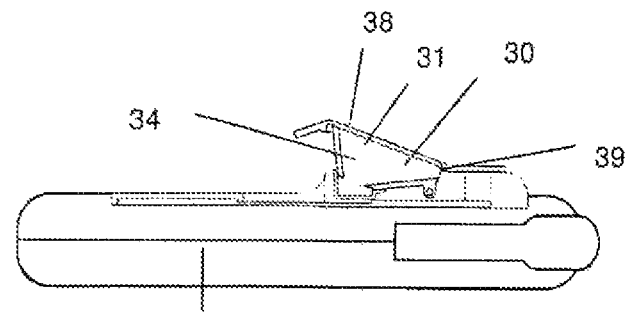
FIG. 12 is a side view of a fourth embodiment, of an assembly.
Figure 13:
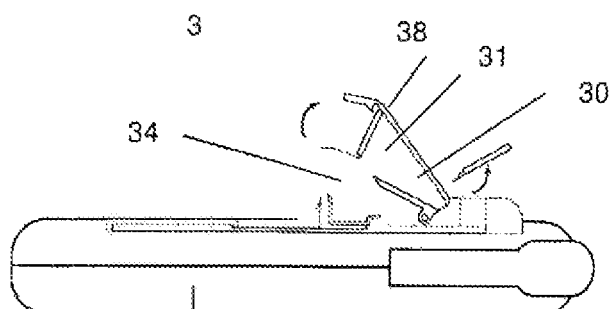
FIG. 13 is a side view of the assembly of FIG. 12.

In other forms illustrated in FIGS. 10 and 11, the collector 14, still in the form of a capillary tube 16, is moveable, between the collection position shown in FIG. 10 and the delivery position shown in FIG. 11 through sliding the collector 14 longitudinally into contact with the test element 9. In this form the user allows fluid uptake into the collector then slides the collector 14 into contact with the test element to allow release of the retained fluid onto the test element.

In other forms illustrated in FIGS. 12 through 19, the collector 14 is in the form of a capillary plate 30 which comprises two substantially parallel plates 31 defining a channel or cavity 32 therebetween.

Figure 14:
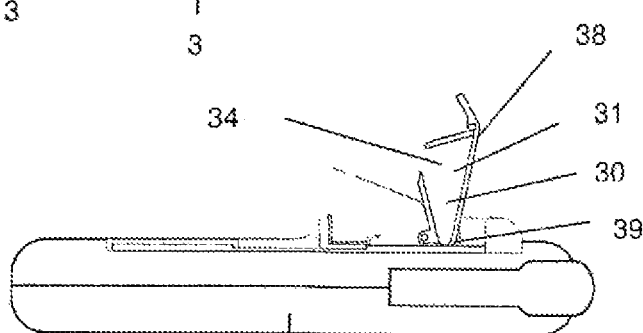
FIG. 14 is a side view of the assembly of FIG. 12.
Figure 16:
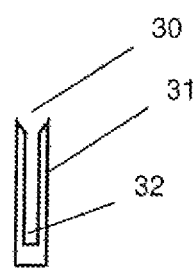
FIG. 16 is a cross section view of a collector of one embodiment of the assembly.
Figure 15:
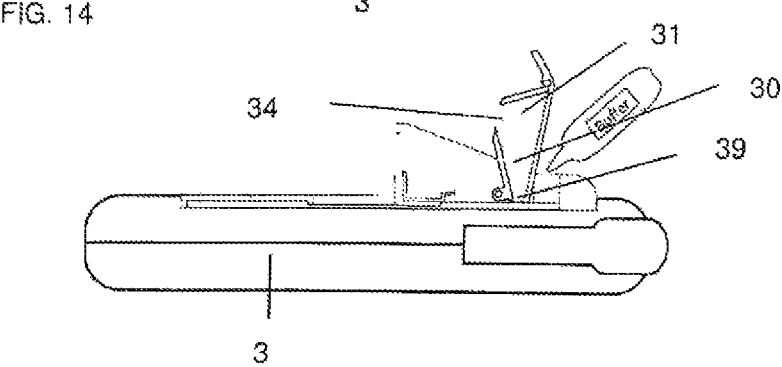
FIG. 15 is a side view of the assembly of FIG. 12.
Figures 17, 19:
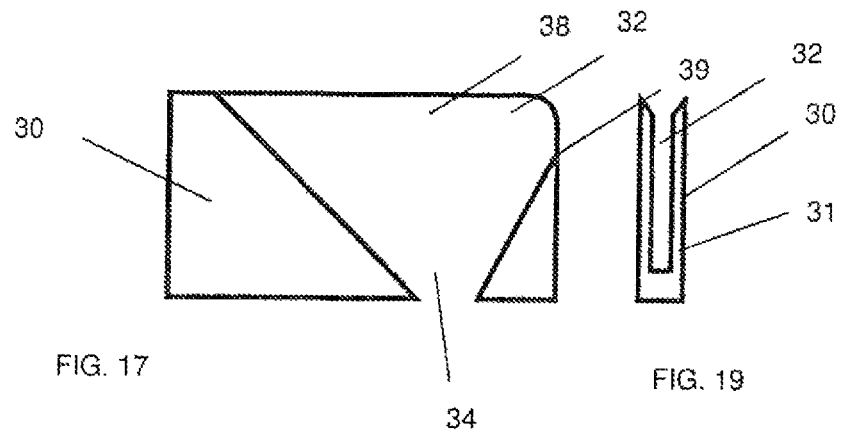
FIG. 17 is a side view of the collector of FIG. 16.
FIG. 19 is an end view of the collector of FIG. 16.
Figure 18:
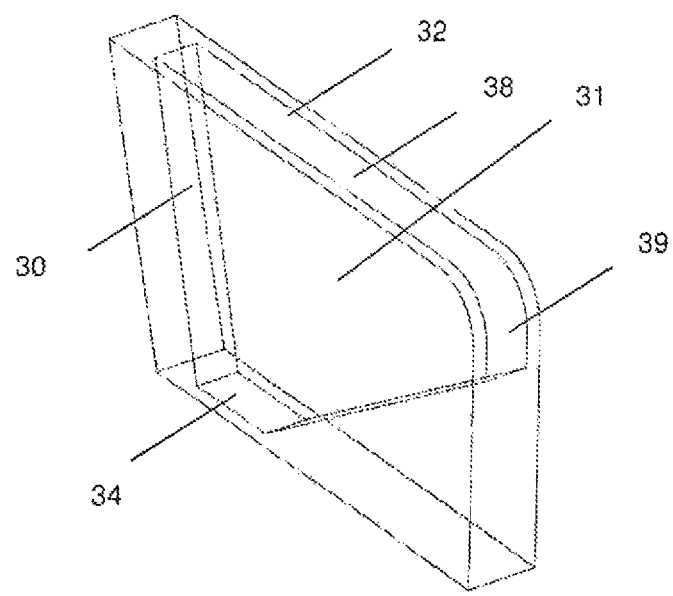
FIG. 18 is a perspective view of the collector of FIG. 16.
Figure 20:
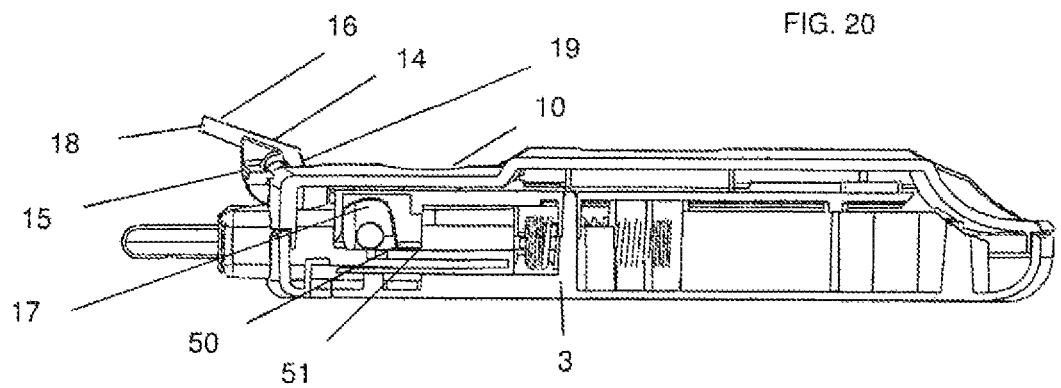
FIG. 20 is a cross-sectional view of a fifth embodiment of an assembly.
Figure 21:
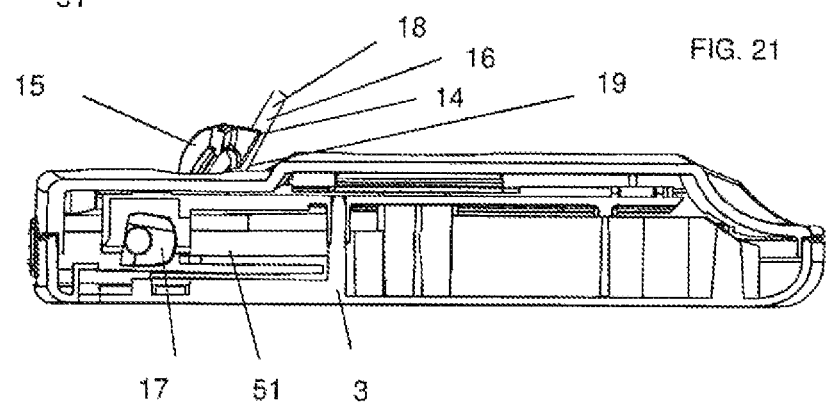
FIG. 21 is a cross-sectional view of the assembly of FIG. 20.
Figure 22:
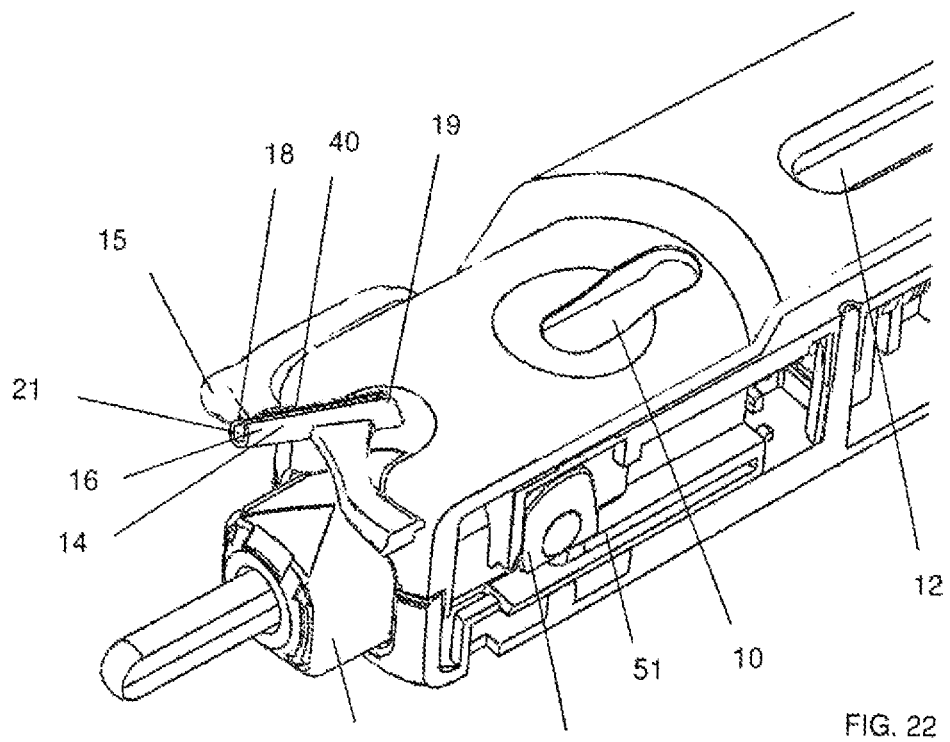
FIG. 22 is a cut away perspective view of the assembly of FIG. 20.
Figure 23:
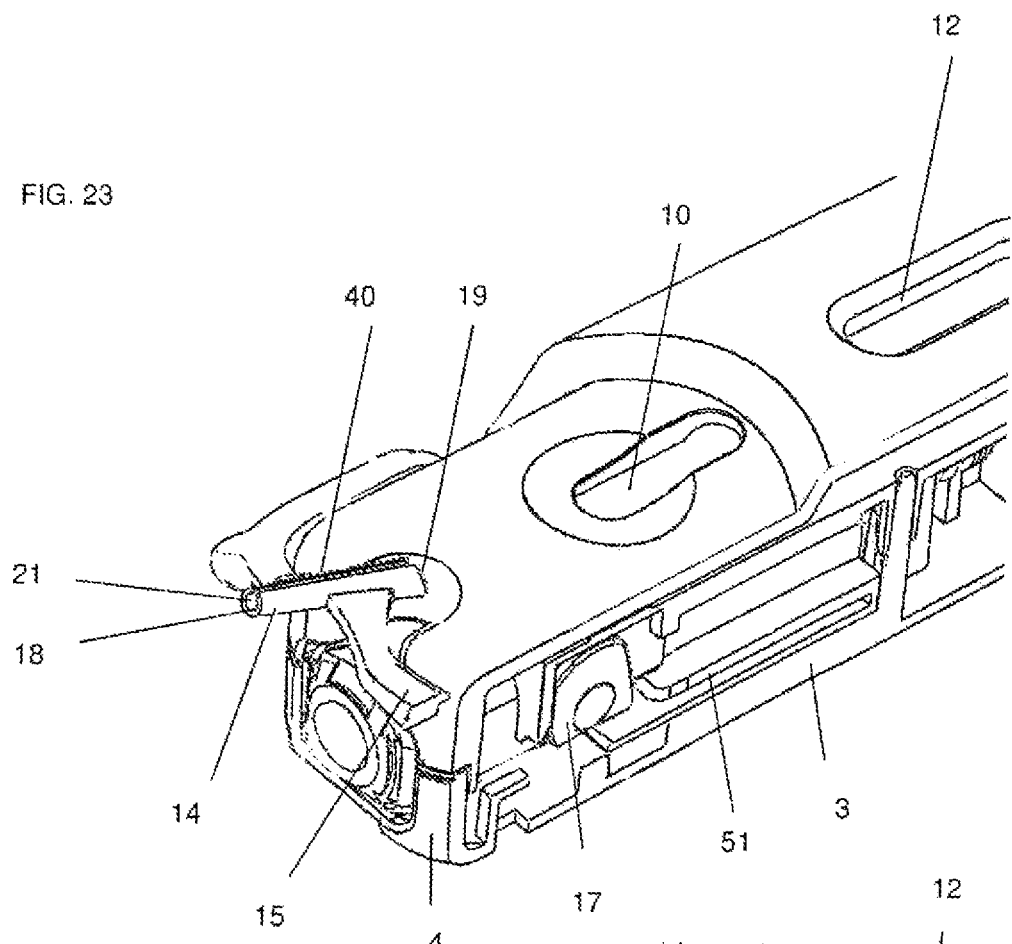
FIG. 23 is a cut away perspective view of the assembly of FIG. 20.
Figure 24:
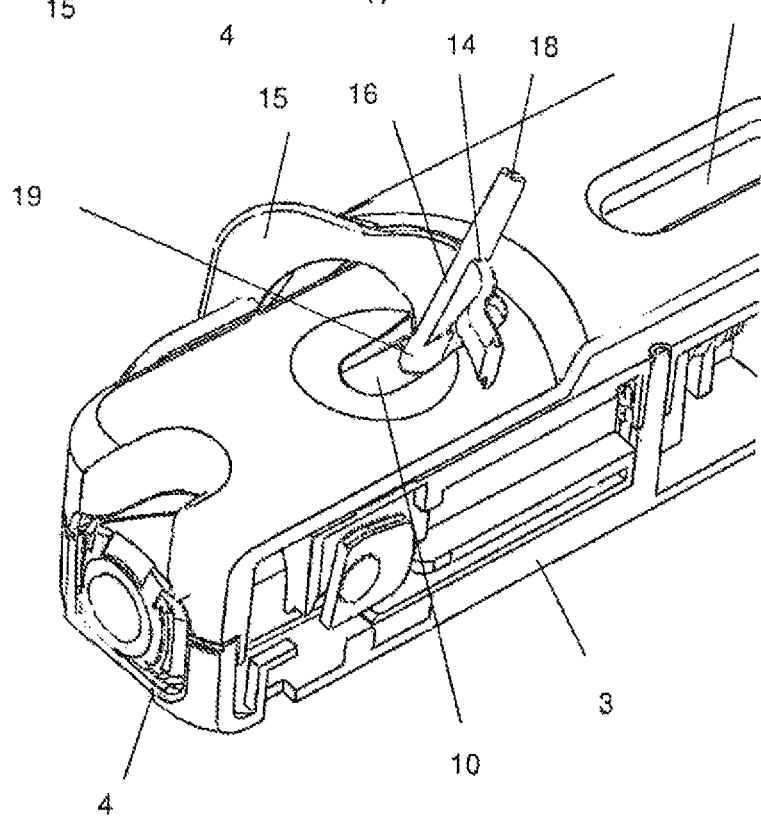

The collector 14 in the form of the capillary plate 30 is shown best in FIGS. 17 through 19 which disclose parallel plates 31 defining a cavity 32 therebetween which is sized and shaped to generate capillary action. A user positions a pierced membrane on collection opening 38 and allows bodily fluid to be taken up into the cavity 32. A ventilation aperture 34 is positioned facing the opening 38 to limit the formation of air bubbles in the cavity as well as reducing problems in the subsequent delivery or release of the fluid due to air entrapment. The user then rotates the capillary plate 30 into the delivery position as shown in FIGS. 14 and 15. In the delivery position the discharge opening 39 contacts the test element (not illustrated in these Figs) allowing release of the fluid onto the test element.

In other forms illustrated in FIGS. 20 through 27, the collector is again in the form of a capillary tube 16. In this form the capillary tube includes a ventilation aperture 40. In the illustrated form the ventilation aperture 40 is in the form of a longitudinally extending slit 41 which extends between the collection opening 18 and the discharge opening 19. The ventilation aperture 40 allows for release of air while the bodily fluid is taken up into the capillary tube 16. This limits the formation of bubbles within the collector 14 which allows for more accurate volume of fluid to be retained in the collector 14.

Figure 27:
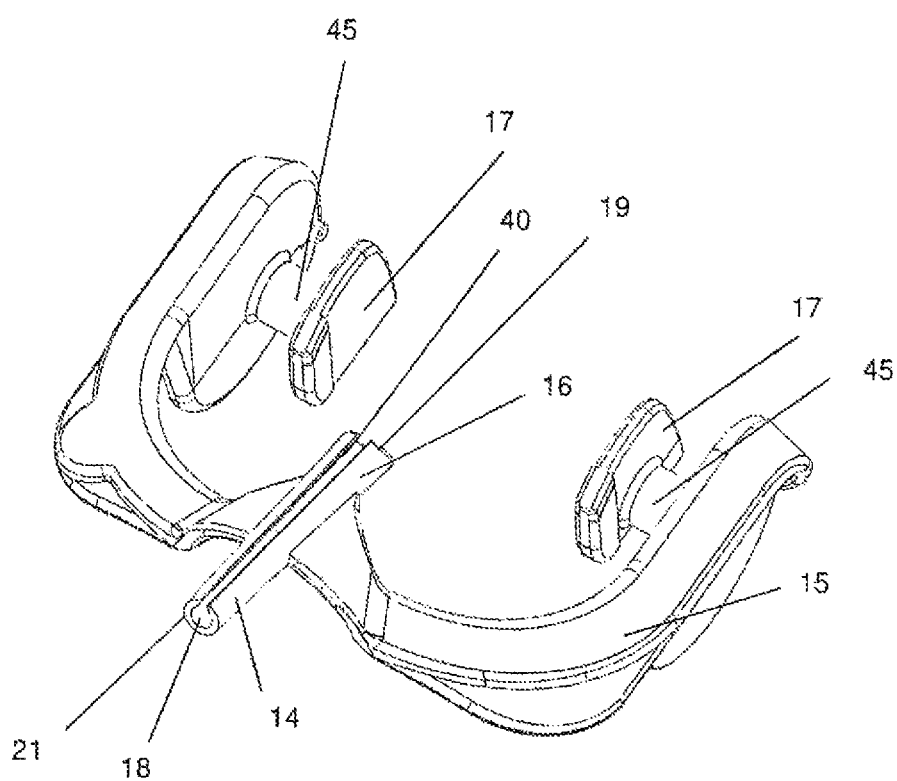
FIG. 27 is a perspective view of a second embodiment of the collector.

The collector 14 and engagement arms 15 are independently shown in FIG. 27 which shows the collector 14 engaged with the engagement arms 15. The engagement arms 15 extend from the collector 14 to engagement points 16 at which the engagement arms are pivotally connected with the housing 3 of the assembly 1 by means, in the illustrated form, of flange 17 and hinge pin 45 which engage the housing 3 such that the flange 17 abuts an internal shoulder or wall in the housing 3. The engagement arms 15 define a curved U or C shape which meets at the collector 14.

FIGS. 19 through 24 show forms in which the collector 14 is moveable between the collection position and the delivery position only after actuation of the membrane penetration device. In the illustrated forms rotation of the collector 14 into the discharge position is prevented by locking mechanism 50 which comprises a locking plate 51 which blocks movement of flange 17 about its axis. The flange 17 includes a flat surface 52 which abuts against locking plate 51 when the locking plate 51 is in a locking position. Actuation of the membrane penetration device 5 to release membrane penetration element 6 effects movement of the locking plate 51 away from the penetration end 4 of the housing 3 and into an unlocked position. This moves the locking plate 51 out of abutment with the flange 17 and allows rotation of the flange 17 about its axis which effects rotation of the collector 14 into the delivery position.

Figure 25:
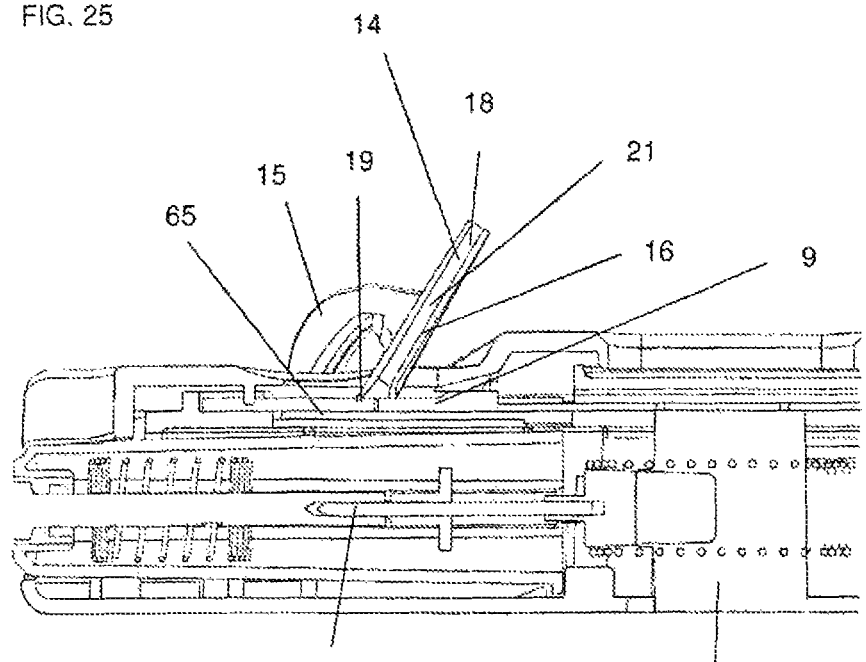
FIG. 25 is a cross-sectional view of the assembly of FIG. 20.
Figure 26:
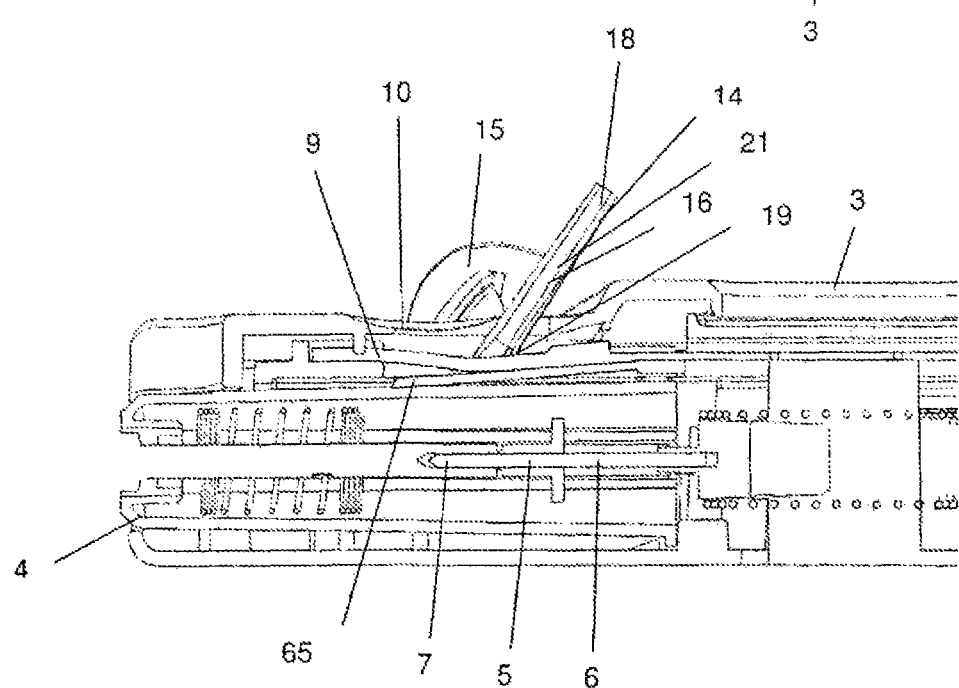
FIG. 26 is a cross-sectional view of the assembly of FIG. 20.

FIGS. 25 and 26 show forms of the assembly in which the movement of the collector into the delivery position is controlled by means of a cantilever effect in order to minimize spillage and protect the test element 9. In the illustrated form the housing includes a slot on either side of the test element 9 to allow for flexion in the engagement arms 15 to take up the force of movement of the collector 14. The assembly 1 further includes a flexion element 65 positioned beneath the test element 9 to allow for flexion of the test element 9 and limit compression of the test element. This allows the collector 14 to stop softly at the test element 9. Compression of the test element can result in the fluid not wicking away from the contact point between the collector 14 and the test element 9 which reduces the accuracy and effectiveness of the assembly. Further, an abrupt stop of the collector 14 against the test element 9 can result in spillage or flicking of the fluid. This feature in some forms has the advantage of soaking up tolerances in the assembly.

FIGS. 28 through 30 show an assembly 1 where the collector 14 in the form of a capillary tube 16 is prevented from rotating into the discharge position. In the illustrated form this prevention is by means of a manual locking plate 60 which is manually slideable between a locking position in which it prevents the collector 14 and engagement arms 15 from rotating as shown in FIG. 28 to a position more distal from the penetration end 4 of the housing 3 which allows rotation of the collector 14 and engagement arms 15 as shown in FIGS. 29 and 30.

Figure 31:
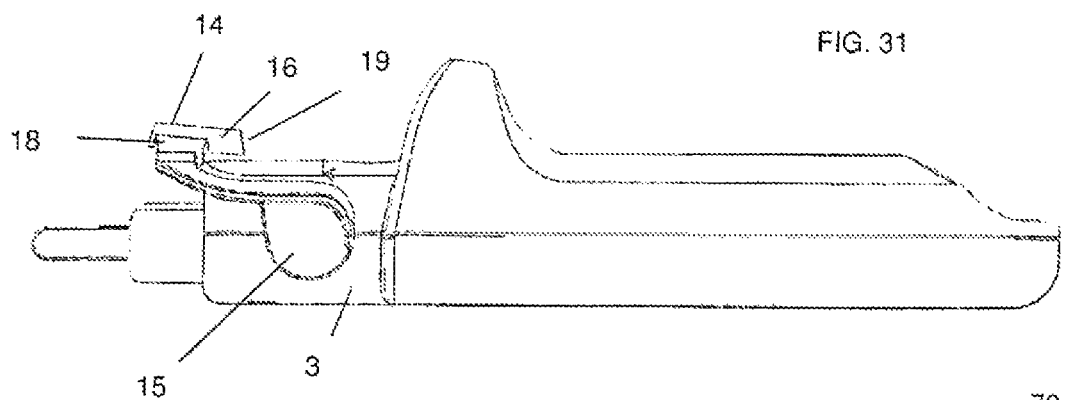
FIG. 31 is a side view of a seventh embodiment of an assembly.
Figure 32:
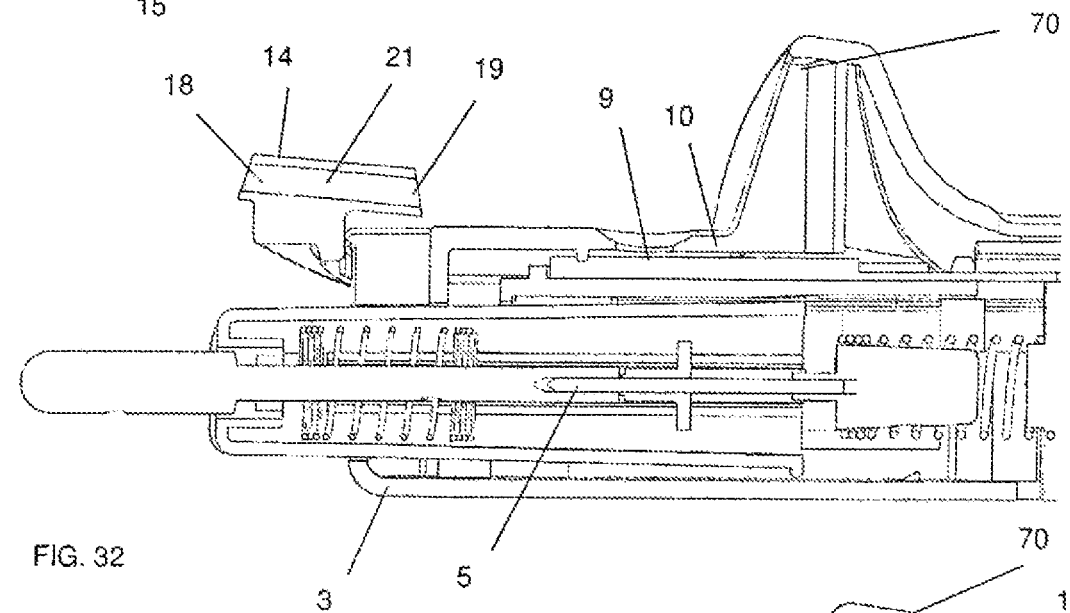
FIG. 32 is a cross-sectional view of the assembly of FIG. 31.
Figure 33:
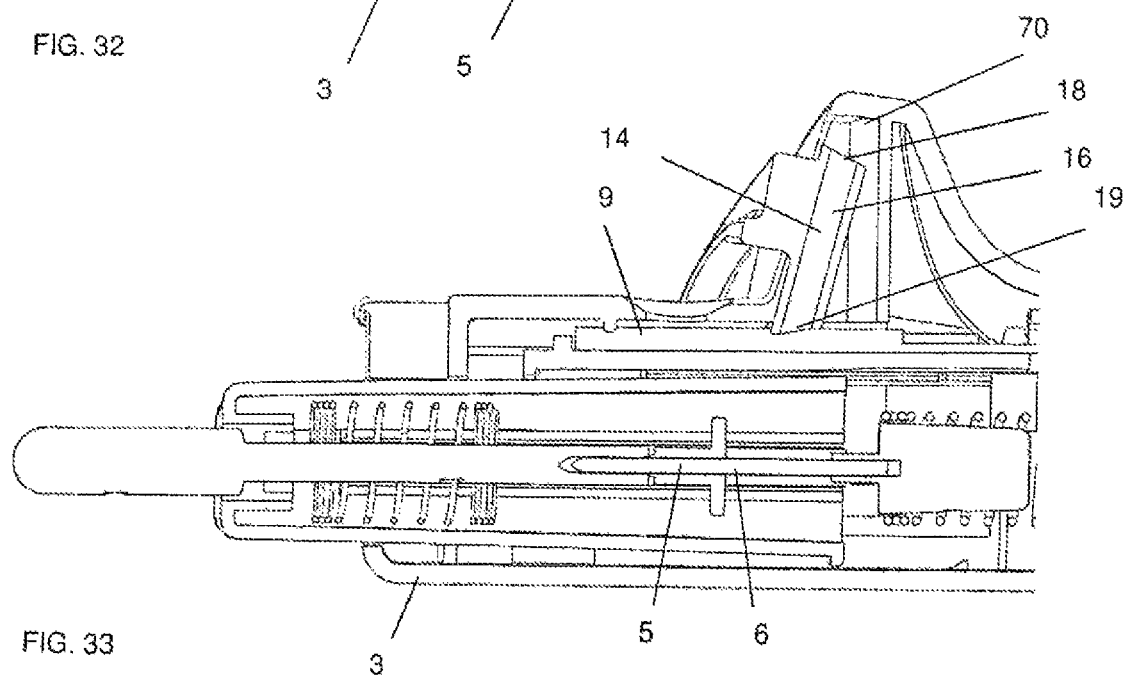
FIG. 33 is a cross-sectional view of the assembly of FIG. 31.

FIGS. 31 through 33 show an assembly 1 in which the collection opening 18 of the capillary tube 16 is moveable into a closed position when delivery of the fluid occurs. In the delivery position as shown in FIG. 33, the collector 14 is located beneath a raised cover 70 which is spaced apart from the delivery window 10 such that when the collector 14 is moved into the delivery position the cover 70 blocks access to the collection opening 18. This effectively blocks a user from maintaining the membrane on the collector and allowing excess fluid to be taken up by the collector.

Figure 34:
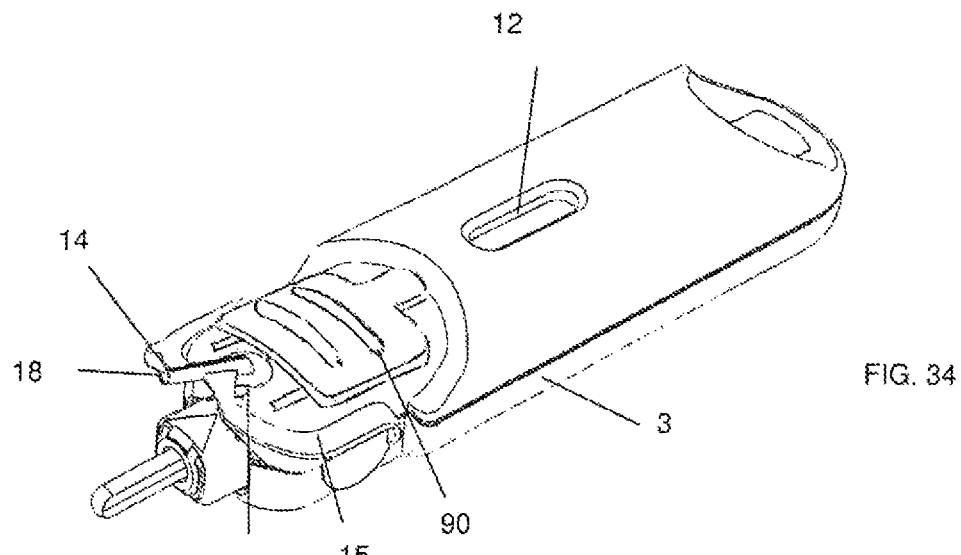
FIG. 34 is a perspective view of an eighth embodiment of the assembly.
Figure 35:
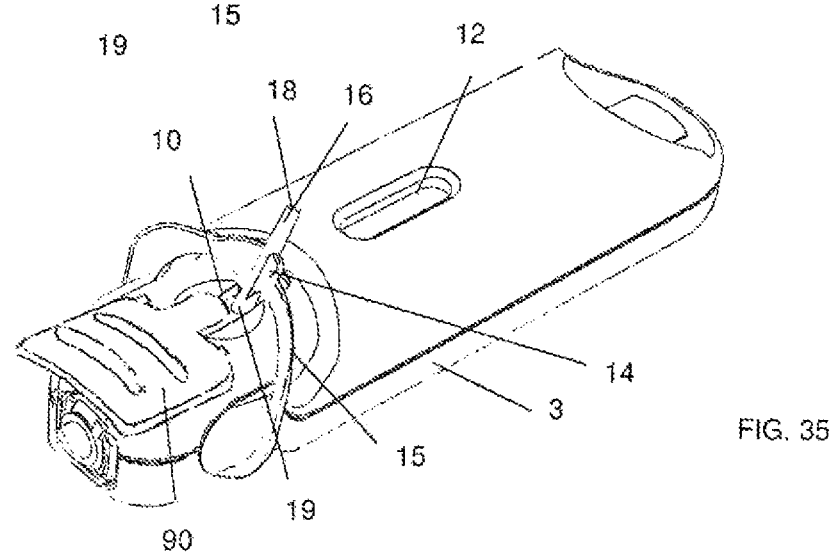
FIG. 35 is a perspective view of the assembly of FIG. 34.
Figure 36:
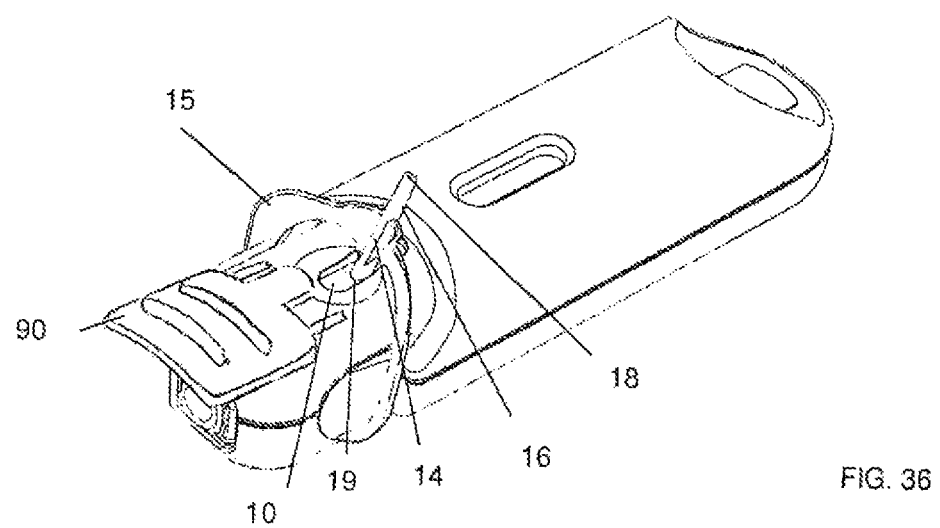
FIG. 36 is a perspective view of the assembly of FIG. 34.
Figure 37:
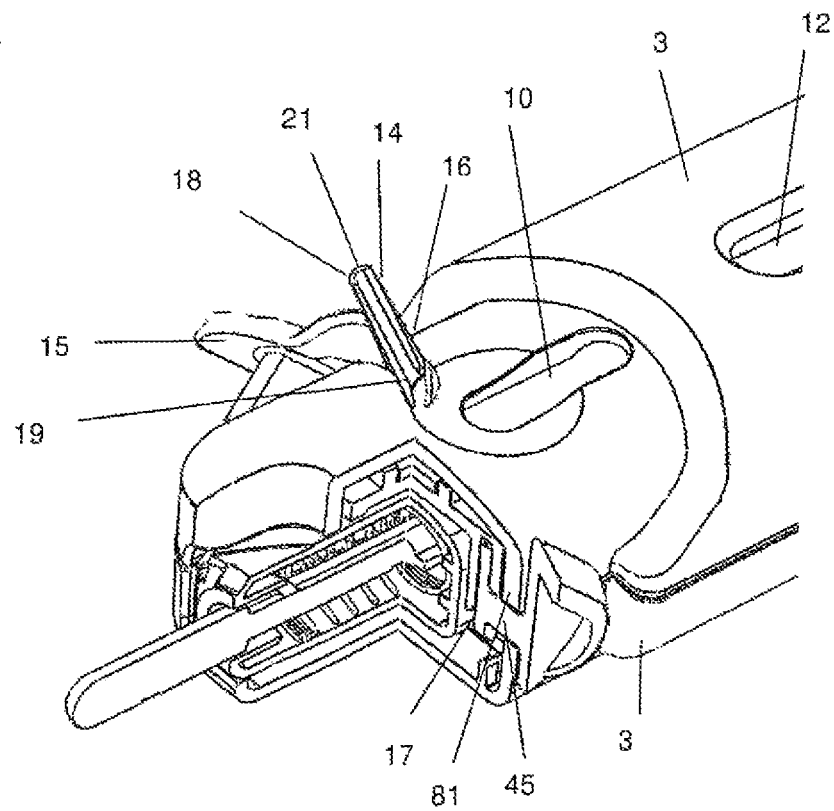
FIG. 37 is a cut away perspective view of a ninth embodiment of an assembly.
Figure 38:
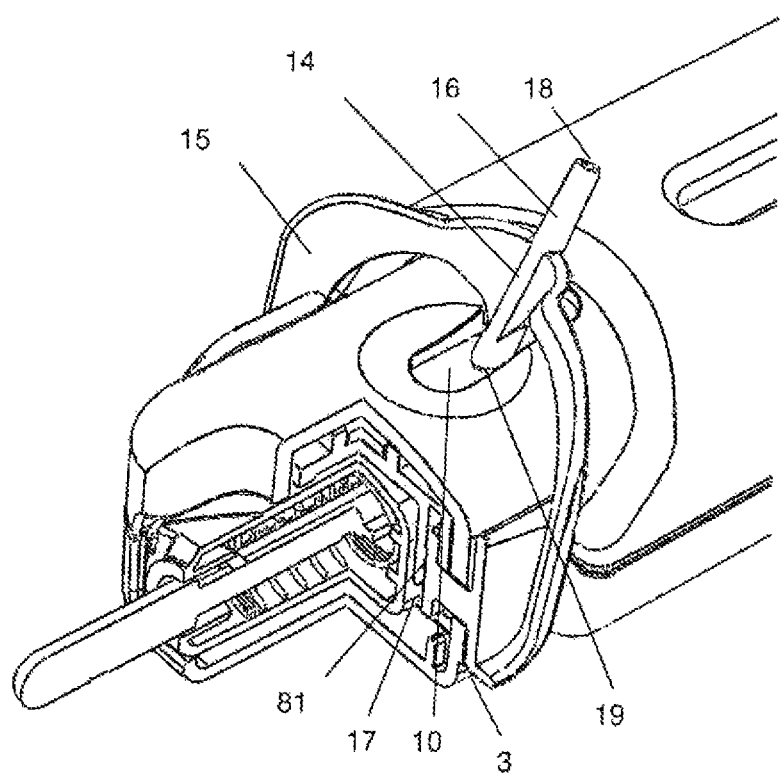
FIG. 38 is a cut away perspective view of the assembly of FIG. 37
Figure 39:
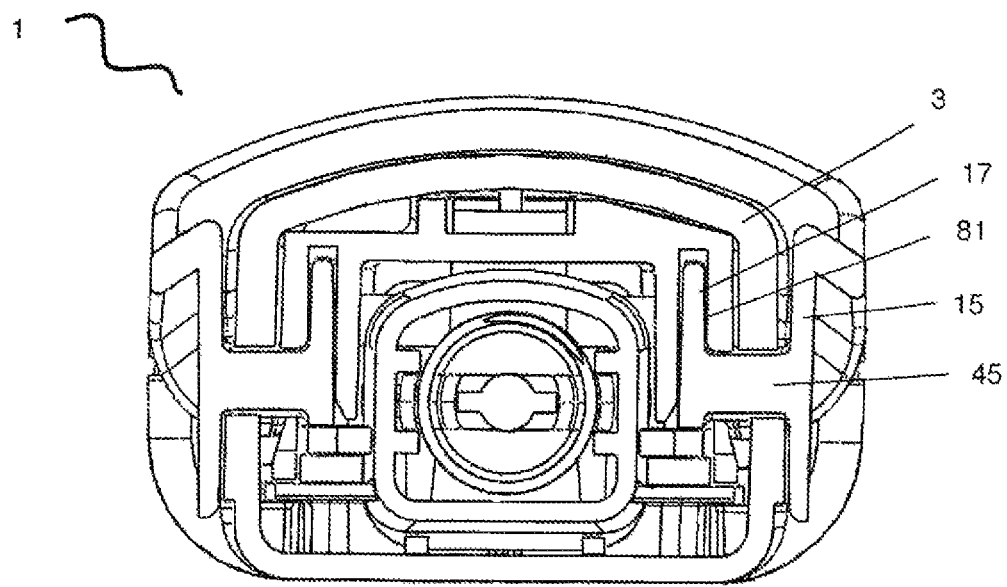
FIG. 39 is a lateral cross-sectional view of a tenth embodiment of the assembly.
Figure 40:
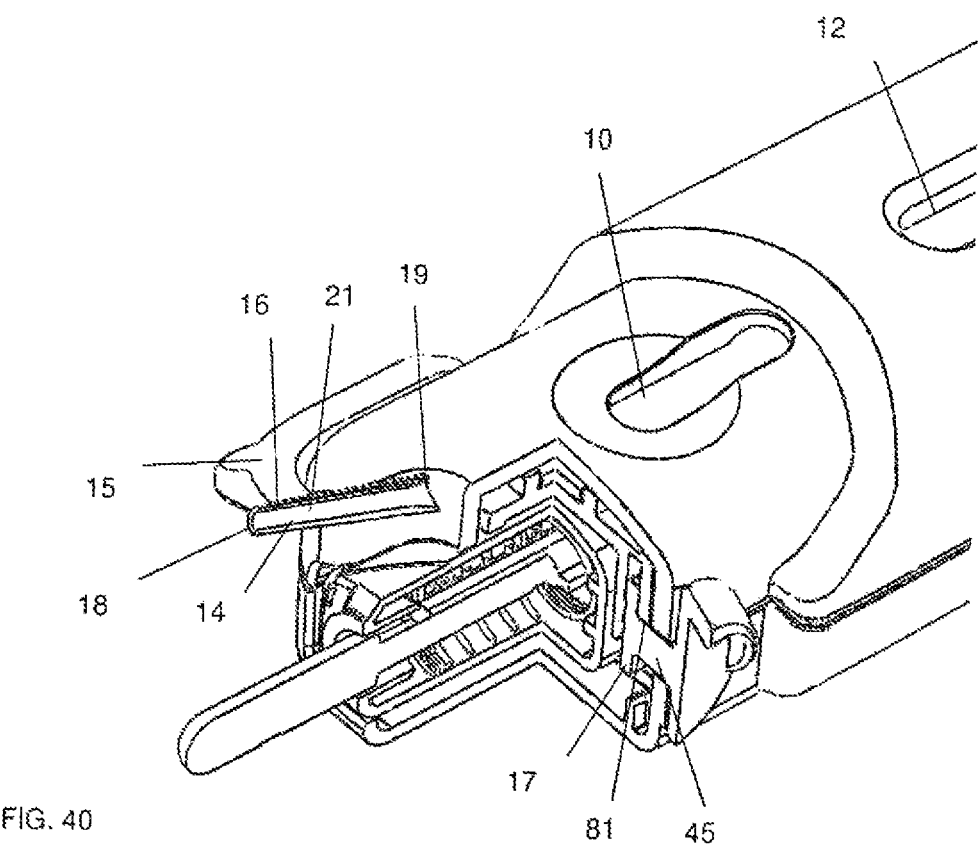
FIG. 40 is a cut away perspective view of the assembly of FIG. 39.
Figure 43:
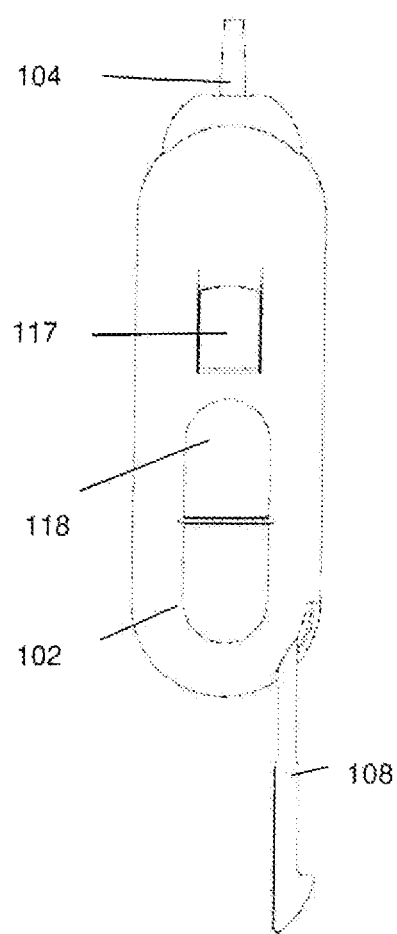
FIG. 43 is a bottom view of the assembly of FIG. 41 with fluid collection element extended.
Figure 42:
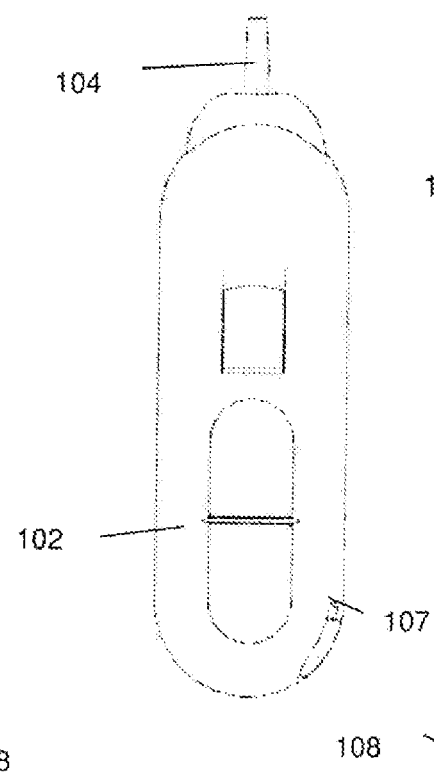
FIG. 42 is a bottom view of the assembly of FIG. 41.
Figure 41:
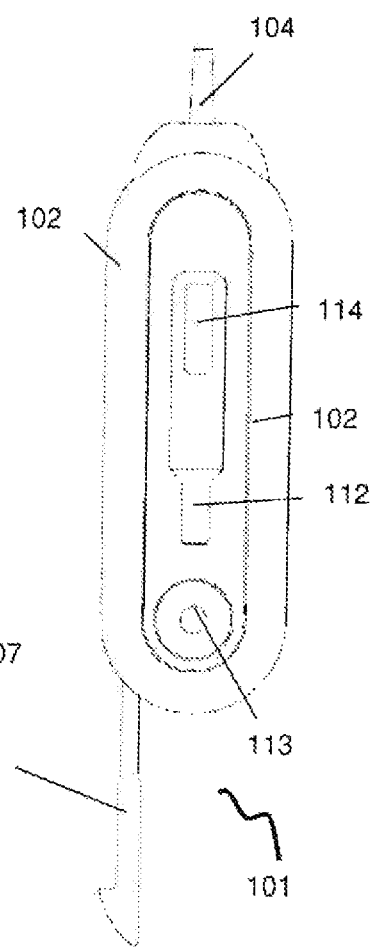
FIG. 41 is a top view of an eleventh embodiment of an assembly.

In some forms as illustrated in FIGS. 34-36, a delivery cover 90 is shown. The delivery cover 90 is moveable between a closed position as shown in FIG. 34 in which the cover 90 blocks access to the delivery window 10 and an open position as shown in FIG. 36. In the illustrated form rotation of the engagement arms 15 effects movement of the delivery cover 90 to allow the collector 14 to contact the test element 9 through the delivery window 10. In not Illustrated forms movement is actuated by the user by, for example, sliding, unclipping, moving or rotating the cover.

In some forms the movement of the collector into the delivery position is coupled with the movement of a delivery cover in order to encourage the correct sequence of steps for a user. In some forms the movement of the collector into the delivery position is coupled with the movement of a collector cover, similarly in order to encourage the correct step sequence.

In some forms as shown in FIGS. 37 through 40, movement of the collector 14 by means of the engagement arms 15 between the collection position and the delivery position is slowed or smoothed through generating a resistance fit between the outer surface 81 of flange 17 and the housing 3 at abutment surface 80. Thus friction between the flange 17 and abutment surface 80 of the housing 3 is utilized to control rotation of the engagement arms limiting the likelihood of spillage of the fluid and reducing the force of the collector 14 on the test element 3.

In at least one form the sampling assembly allows a user to collect a bodily fluid from the site of membrane penetration without additional steps such as finding a collection device or container and expressing the fluid onto the device. The fluid collection element allows for easy and safe fluid collection from the piercing site. In some forms the simplicity is increased by allowing a user to prepare the site and removing the necessity of finding an alcohol wipe and a drying or cleansing wipe for treatment afterwards. This significantly simplifies the process of collecting blood either for a health care professional or for a home user. In at least another form, the assembly allows a user to collect a bodily fluid with a fluid collection element such as a capillary tube, pipette, reservoir or looped wand and deposit it at a collection point where it and a physiologically acceptable solution are brought into contact with a test material. In one form the fluid collection element is integrated and positioned for convenient sample collection near the blood collection site. In another form the fluid collection element is moveable between a retained position and an operative position. In one form the fluid collection element is moveable between an operative position for collection of a bodily fluid and a delivery position for delivery of the fluid sample to a diagnostic device.

In use inn one form a user obtains a sterile wipe from the composite system, cleans a penetration site, activates the piercing element to penetrate the user's skin, before or after moving the fluid collection, element into an operative position. The user will ordinarily wipe away a first drop of blood using a wipe then position the fluid collection element to collect the bodily fluid released from the penetration site. The user then, if necessary, positions the fluid collection element to release the bodily fluid onto a collection window. The user then actuates a buffer or diluent delivery to carry the fluid across a test or diagnostic strip. The sampling assembly then displays a result of the diagnostic test.

In not illustrated forms, delivery onto the test element is by means of dropping, squeezing, spraying or other alternative delivery methods that may or may not include contact with the test element. For example, in some forms the collector comprises a pipette including a bulb which is squeezed to deliver the fluid to the test element.

In some not illustrated forms the collector is adapted to contain, a substance such as a diluent, a buffer, a reagent, a physiologically acceptable solution, a reactant or other solutions, powders, fluids or substances appropriate for an aspect of the process of testing a bodily fluid. In some not illustrated forms the collector comprises a reservoir for containing a substance.

In some not illustrated forms, the reservoir can receive substances either prior or pest uptake of the sample.

In some not illustrated forms, the collector includes one opening which acts as collection opening and discharge opening. In some forms the collector also include a ventilation aperture.

In an embodiment as shown in FIG. 41 through 45, disclosed is an assembly 101 for collecting and handling a sample of a bodily fluid. The assembly 101 is described, with reference to collecting and handling blood samples, though a person skilled in the art will be aware that other bodily fluids may be collected using the assembly.

The assembly 101 comprises a body 102 comprising a membrane piercing element (not illustrated) which extends from a membrane piercing point 104 to allow a user to pierce skin or another membrane. The membrane piercing element comprises a lancet such as a needle or blade or other sharp which disposed prior to use within the body 102. The lancet is moveable from a housed position in which the lancet is substantially disposed within the body 102. In this position the lancet is protected by the body 102. This position is shown in the Figures. The lancet is moveable to an extended position (not illustrated) in which the lancet extends at least partly from the body 102. In this position the tip of the lancet is positioned outside the body 102 such that a user can prick, pierce, cut or otherwise penetrate the skin with the lancet.

The movement of the lancet from the housed position to the extended position is performed with sufficient force to pierce the skin of a user such that if the body 102 is positioned against the skin of the user and movement of the lancet between the housed and the extended position is actuated the skin will be pierced by the lancet.

The sampling assembly 101 further comprises a collector retainer 107 which is disposed within the body 102. The collector retainer 107 is composed of a cavity extending into the body 102 however a person skilled in the art will be aware that other configurations will allow for retention of a fluid collection element such as a capillary tube, pipette, reservoir or looped wand. For example, a clip, sheath or hinge can be utilised, as the fluid collection element retainer. Alternatively a hinge could be utilised.

A fluid collection element in the form of a capillary tube 108 is removably positioned within the fluid collection element retainer 107. The capillary cube 108 is configured to allow capillary action and is composed of any material allowing sufficient wetting of the capillary interior for capillary action of a bodily fluid to take place. However a person skilled in the art will be aware that alternative embodiments not utilizing capillary action will be available.

In use, a user removes the capillary tube 108 from the retainer 107 before or after locating the piercing membrane point against the skin at the site where the blood is to be sampled. The user actuates the device such that the lancet moves from the housed position to the extended position, piercing the skin and allowing blood to be expressed. The lancet then returns automatically to the housed position.

Activation of the device between the housed position and the extended position occurs through depression of the membrane piercing point 104 into the body by the user's finger although a person skilled in the field will be aware that a separate actuation button or lever may be utilised.

The user then utilizes the capillary tube 108 and positions it such that blood which is expressed from the piercing is taken up by the tube 108 merely by contacting the blood with the tube 8. A particular amount of blood can be stored by the tube 108 depending upon the length of the tube, making the device suitable with quantitative diagnostic applications.

The user then positions the capillary tube over the bodily fluid collection point 112 and bodily fluid, in this case blood, is delivered to the collection point.

In not illustrated forms the fluid collection element is a pipette, a reservoir or a wand having a loop for collection of fluid. A person skilled in the art will be aware that other fluid collection elements designed to collect blood from a user and transfer it to the fluid collection point.

The assembly 101 further comprises a buffer reservoir for holding a physiologically acceptable solution such as a buffer or diluent for supporting the blood or other bodily fluid and aiding in conveying the bodily fluid. A solution delivery actuator 113 is positioned on the assembly 101. Actuation of the solution delivery actuator 113 releases the buffer solution from an internal reservoir and delivers it to a diagnostic device or assay including but not limited to lateral flow test strips, vertical flow test strips or agglutination and solid-phase technologies.

The diagnostic device further includes a results window 114 which is positioned for easy viewing of the results of any diagnostic test performed.

The buffer or diluent reservoir and test strip are positioned internally to the device and therefore not illustrated in the Figures.

A sterile wipe locator 117 and an adhesive plaster locater 118 are positioned on one side of the body 102 to allow for ease of access for a user.

In not illustrated embodiments, the fluid collection element is retained by the sampling assembly in a position where the user can contact the penetration site to the fluid collection element after piercing without removing the fluid collection element from the fluid collection element retainer. For example, the fluid collection element may be oriented to allow access to the fluid collection element without movement of the fluid collection element. The fluid collection element may be oriented to deliver the fluid to the collection point without movement of the fluid collection element.

Alternatively the fluid collection element may be moveable between an inoperative and an operative position without removing the fluid collection element from the fluid collection element retainer. In one example the fluid collection element may be hingedly retained or in an alternative the fluid collection element may be retained by a cord or biasing means such as a spring.

In a further not illustrated embodiment, the fluid collection element may be associated with a lancet or other penetration device for fluid collection. The fluid collection element can then be utilised to collect and transport the fluid for testing and diagnosis at a separate location.

Throughout the detailed description, the membrane penetrating element has been referred to and described in respect of a lancet as illustrated, however persons skilled in the art will be aware that the lancet could be any piercing, slicing, cutting, puncturing or pricking element which allows a user to penetrate a membrane such as the skin to allow a fluid sample to be released.

Throughout the detailed description reference to capillary action is used to refer to the taking up of a fluid through adhesion of a fluid with a surface of the collector and/or surface tension of that fluid.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

Variations and modifications may be made to the parts previously described without departing from the spirit or ambit of the invention.

The invention claimed is:

1. A single use assembly for sampling bodily fluid, the assembly comprising a membrane penetrating element for penetrating a bodily membrane to release a supply of bodily fluid; an engagement arm; and a collector reservoir positioned on the engagement arm, the membrane penetrating element being positioned separate from and outside of the collector reservoir and the engagement arm, the collector reservoir being configured to adopt a collection position to take up and store a sample of released bodily fluid from the supply of bodily fluid in the collector reservoir and a delivery position to deliver the stored sample from the collector reservoir to a test element, the collector reservoir having a predefined sample volume, wherein the collector reservoir is not in fluid communication with the test element in the collection position and is not in fluid communication with the supply of bodily fluid in the delivery position; wherein the collector reservoir is configured to move between the collection position and the delivery position by movement of the engagement arm; and wherein the assembly is configured such that movement of the collector reservoir between the collection position and the delivery position is controlled bar movement of the engagement arm.

2. The assembly according to claim 1, wherein the collector reservoir is configured to take up the sample of released bodily fluid by capillary action.

3. The assembly according to claim 1, wherein the collector reservoir comprises a tube including a ventilation aperture.

4. The assembly according to claim 3, wherein the tube includes a collection opening and a discharge opening, and the ventilation aperture is a longitudinal slot extending from the collection opening to the discharge opening.

5. The assembly according to claim 1, wherein the collector reservoir is adapted in the delivery position to deliver the sample to a specific, predefined position on the test element.

6. The assembly according claim 1, wherein the collector reservoir is operatively adapted to move from the collection position to the delivery position by one or more of pivoting, sliding, rotating and translating of the engagement arm.

7. The assembly according to claim 1 wherein the collector reservoir is inhibited from moving into the delivery position by a locking mechanism until after the membrane penetrating element has been actuated.

8. The assembly according to claim 1, further including a retainer adapted to retain the collector reservoir.

9. The assembly according to claim 8, wherein the retainer is selected from the group consisting of a clip engaged with the assembly, a pivotable engagement, and a cavity.

10. The assembly according to claim 1, wherein the assembly further includes an internal storage for a solution and an actuator adapted to release the solution from the internal storage to the test element.

* * * * *